US009662606B2

(12) United States Patent
Inubushi et al.

(10) Patent No.: US 9,662,606 B2
(45) Date of Patent: May 30, 2017

(54) METAL COMPLEX AND ADSORBENT MATERIAL, STORAGE MATERIAL, AND SEPARATING MATERIAL COMPRISING SAME

(75) Inventors: Yasutaka Inubushi, Kurashiki (JP); Chikako Ikeda, Kurashiki (JP); Takashi Hori, Kurashiki (JP)

(73) Assignee: KURARAY CO., LTD., Kurashiki-shi (JP)

( * ) Notice: Subject to any disclaimer, the term of this patent is extended or adjusted under 35 U.S.C. 154(b) by 592 days.

(21) Appl. No.: 14/238,662

(22) PCT Filed: Aug. 8, 2012

(86) PCT No.: PCT/JP2012/070172
§ 371 (c)(1),
(2), (4) Date: Feb. 12, 2014

(87) PCT Pub. No.: WO2013/024761
PCT Pub. Date: Feb. 21, 2013

(65) Prior Publication Data
US 2014/0190436 A1    Jul. 10, 2014

(30) Foreign Application Priority Data
Aug. 17, 2011  (JP) ................................ 2011-178510

(51) Int. Cl.
| | | |
|---|---|---|
| B01D 53/04 | (2006.01) | |
| B01D 53/02 | (2006.01) | |
| C07C 63/28 | (2006.01) | |
| B01J 20/22 | (2006.01) | |
| B01J 20/30 | (2006.01) | |
| B01J 20/34 | (2006.01) | |
| B01D 53/047 | (2006.01) | |
| C01B 3/56 | (2006.01) | |
| C07C 65/21 | (2006.01) | |
| C07F 3/00 | (2006.01) | |

(52) U.S. Cl.
CPC ......... *B01D 53/0462* (2013.01); *B01D 53/02* (2013.01); *B01D 53/047* (2013.01); *B01J 20/223* (2013.01); *B01J 20/226* (2013.01); *B01J 20/3085* (2013.01); *B01J 20/3425* (2013.01); *B01J 20/3483* (2013.01); *B01J 20/3491* (2013.01); *C01B 3/56* (2013.01); *C07C 63/28* (2013.01); *C07C 65/21* (2013.01); *C07F 3/003* (2013.01); *B01D 2253/204* (2013.01); *B01D 2256/18* (2013.01); *B01D 2257/102* (2013.01); *B01D 2257/104* (2013.01); *B01D 2257/304* (2013.01); *B01D 2257/406* (2013.01); *B01D 2257/502* (2013.01); *B01D 2257/504* (2013.01); *B01D 2257/702* (2013.01); *B01D 2257/80* (2013.01); *C01B 2203/042* (2013.01); *C01B 2203/043* (2013.01); *C01B 2203/0475* (2013.01); *Y02C 10/08* (2013.01); *Y02P 20/152* (2015.11); *Y02P 20/51* (2015.11); *Y02P 30/30* (2015.11)

(58) Field of Classification Search
CPC ........ C01B 2203/042; C01B 2203/043; C01B 2203/0475; C01B 3/56; B01D 53/02; B01D 53/0462; B01D 53/047; B01J 20/223; B01J 20/226; B01J 20/3085; B01J 20/3425; B01J 20/3483; B01J 20/3491; C07C 63/28; C07C 65/21; C07F 3/003
See application file for complete search history.

(56) References Cited

U.S. PATENT DOCUMENTS 7,431,151 B2 * 10/2008 Hosoe .................... B82Y 30/00
                                                              206/7
2012/0312164 A1    12/2012 Inubushi et al.

FOREIGN PATENT DOCUMENTS

| JP | 2000 109485 | 4/2000 |
|---|---|---|
| JP | 2001 348361 | 12/2001 |
| JP | 2003 342260 | 12/2003 |
| JP | 2011 68631 | 4/2011 |

(Continued)

OTHER PUBLICATIONS

Chun et al., "Synthesis, X-ray Crystal Structures, and Gas Sorption Properties of Pillared Square Grid Nets Based on Paddle-Wheel Motifs: Implications for Hydrogen Storage in Porous Materials," Chem. Eur. J. 2005, 11, 3521-3529.*
Li et al., "Selective gas adsorption and separation in metal-organic frameworks," Chem. Soc. Rev. 2009, 38, 1477-1504.*
U.S. Appl. No. 14/410,681, filed Dec. 23, 2014, Inubushi, et al.
U.S. Appl. No. 14/411,598, filed Dec. 29, 2014, Inubushi, et al.
U.S. Appl. No. 14/762,733, filed Jul. 22, 2015, Inubushi, et al.
Combined Chinese Office Action and Search Report issued Sep. 3, 2014 in Patent Application No. 201280040035.7 (with English language translation and English translation of categories of cited documents).

(Continued)

*Primary Examiner* — Paul A Zucker
*Assistant Examiner* — Mark Luderer
(74) *Attorney, Agent, or Firm* — Oblon, McClelland, Maier & Neustadt, L.L.P.

(57) ABSTRACT

The problem of providing a metal complex having excellent gas adsorption performance, gas storage performance, and gas separation performance is solved by a metal complex comprising a dicarboxylic acid compound (I) including 20 to 99 mole % of a dicarboxylic acid compound (I-1) selected from terephthalic acid derivatives having an electron-donating group in the 2nd position such as 2-methoxyterephthalic acid, 2-methylterephthalic acid, and terephthalic acid, and 80 to 1 mole % of a dicarboxylic acid compound (I-2) selected from terephthalic acid derivatives having an electron-withdrawing group in the 2nd position such as 2-nitroterephthalic acid, 2-fluoroterephthalic acid, 2-chloroterephthalic acid, 2-bromoterephthalic acid, and 2-iodoterephthalic acid; at least one kind of metal ion selected from metal ions belonging to Group 2 and Groups 7 to 12 of the periodic table; and an organic ligand capable of bidentate binding to the metal ion.

18 Claims, 20 Drawing Sheets

(56) References Cited

FOREIGN PATENT DOCUMENTS

| JP | 2011 83755 | 4/2011 |
|---|---|---|
| JP | 2011 190256 | 9/2011 |
| WO | WO 2010/148296 A2 | 12/2010 |

OTHER PUBLICATIONS

Chen, B. et al., "A Microporous Metal-Organic Framework for Gas-Chromatographic Separation of Alkanes" Angew. Chem. Int. Ed., vol. 45, No. 9, pp. 1390-1393, 2006.

Chun, H. et al., "Synthesis, X-ray Crystal Structures, and Gas Sorption Properties of Pillared Square Grid Nets Based on Paddle-Wheel Motifs: Implications for Hydrogen Storage in Porous Materials" Chem. Eur. J., vol. 11, No. 12, pp. 3521-3529, 2005.

Yamada, T. et al., "Porous Interpenetrating Metal-Organic Frameworks with Hierarchical Nodes" Crystal Growth & Design., vol. 11, No. 5, pp. 1798-1806, 2011.

International Search Report Issued Oct. 2, 2012 in PCT/JP12/070172 Filed Aug. 8, 2012.

* cited by examiner

METAL COMPLEX AND ADSORBENT MATERIAL, STORAGE MATERIAL, AND SEPARATING MATERIAL COMPRISING SAME

TECHNICAL FIELD

The present invention relates to a metal complex and to an adsorbent material, a storage material, and a separating material made of the metal complex. More specifically, the present invention relates, to a metal complex composed of two kinds of dicarboxylic acid compounds selected from specific dicarboxylic acid compounds, at least one kind of metal ion, and an organic ligand capable of bidentate binding to the metal ion. The metal complex of the present invention is suitable for an adsorbent material, a storage material, or a separating material for adsorbing, storing, or separating carbon dioxide, hydrogen, carbon monoxide, oxygen, nitrogen, hydrocarbons having from 1 to 4 carbon atoms, noble gases, hydrogen sulfide, ammonia, water vapor, organic vapor, or the like.

BACKGROUND ART

In the fields of deodorization, exhaust gas treatment, and the like, various adsorbent materials have so far been developed. Activated carbon is a representative example of these, and it has been used widely in various industries for the purpose of air cleaning, desulfurization, denitrification, or removal of harmful substances by making use of its excellent adsorption performance. In recent years, demand for nitrogen has been increasing, for example, in semiconductor manufacturing processes and the like. Such nitrogen is produced from air by using molecular sieving carbon according to the pressure swing adsorption process or temperature swing adsorption process. Molecular sieving carbon is also used for separation and purification of various gases such as purification of hydrogen from a cracked methanol gas.

When a mixture of gases is separated according to the pressure swing adsorption process or temperature swing adsorption process, it is common practice to separate it based on the difference between the gases in equilibrium adsorption amount or rate of adsorption to molecular sieving carbon or zeolite used as a separation adsorbent material. When the mixture of gases is separated based on the difference in equilibrium adsorption amount, conventional adsorbent materials cannot selectively adsorb thereto only the gas to be removed, and the separation coefficient decreases, making it inevitable that the size of the apparatus used therefor increases. When the mixture of gases is separated into individual gases based on the difference in rate of adsorption, on the other hand, only the gas to be removed can be adsorbed, although it depends on the kind of gas. It is necessary, however, to alternately carry out adsorption and desorption, and also in this case, the apparatus used therefor should be larger.

On the other hand, as an adsorbent material providing superior adsorption performance, there has also been developed a coordination polymer undergoing a change in dynamic structure when exposed to external stimulation. When this novel coordination polymer undergoing a change in dynamic structure is used as a gas-adsorbent material, it does not adsorb a gas until a predetermined pressure, but it starts gas adsorption at a pressure exceeding the predetermined pressure. In addition, a phenomenon is observed in which the adsorption starting pressure differs depending on the nature of the gas.

Application of these phenomena to adsorbent materials used in a gas separation apparatus employing a pressure swing adsorption system enables very efficient gas separation. It can also decrease the pressure swing width, contributing to energy savings. Further, it can contribute to size reduction of the gas separation apparatus, making it possible to increase competitiveness in terms of costs when a high-purity gas is put on the market as a product. Moreover, even if the high-purity gas is used in a company's own plant, the costs paid for the equipment requiring a high-purity gas can be reduced, resulting in a reduction of manufacturing costs of the final product.

At present, however, further reducing the apparatus size is desired for cost reduction. To this end, further improvement of the degree of separation is desired.

Further, Patent Document 1 discloses a coordination polymer composed of a terephthalic acid derivative, a metal ion, and an organic ligand capable of bidentate binding to the metal ion. However, Patent Document 1 only discloses, in Examples, a coordination polymer composed of a terephthalic acid, a copper ion, and pyrazine, and it is completely silent about the effect conducive to the gas adsorption behavior provided by a substituent group that terephthalic acid includes.

Patent Document 2 discloses a coordination polymer composed of a terephthalic acid derivative, a metal ion, and an organic ligand capable of bidentate binding to the metal ion. However, Patent Document 2 only discloses, in Examples, a coordination polymer composed of a terephthalic acid, a copper ion, and 1,4-diazabicyclo[2.2.2]octane, and it is completely silent about the effect conducive to the gas adsorption behavior provided by a substituent group that terephthalic acid includes.

Patent Document 3 discloses a coordination polymer composed of terephthalic acid, a metal ion, and 4,4'-bipyridyl. However, it is completely silent about the effect conducive to the gas adsorption behavior provided by a substituent group that terephthalic acid includes.

Patent Document 4 discloses a porous organometal complex for adsorbing gas formed by the coordination bond of a metal ion, a dicarboxylic acid, and an aromatic heterocyclic compound having a nitrogen atom capable of bidentate binding to the metal ion, wherein the porous organometal complex has a porous structure. However, Patent Document 4 only discloses, in Examples, a coordination polymer composed of a terephthalic acid, a copper ion, and 1,4-di(4-pyridyl) benzene, and it is completely silent about the effect conducive to the gas adsorption behavior provided by a substituent group that terephthalic acid includes.

Patent Document 5 discloses a coordination polymer composed of a 1 to 30 mol % of a terephthalic acid derivative that may include an electron-donating group in the 5th position, 99 to 70 mol % of isophthalic acid derivative that includes an electron-withdrawing group in the 5th position, a metal ion and an organic ligand capable of bidentate binding to the metal ion. However, when the metal complex disclosed in Patent Document 5 was evaluated, it was found that its performance was not satisfactory.

CITATION LIST

Patent Documents

Patent document 1: Japanese Unexamined Patent Application Publication No. 2000-109485

Patent document 2: Japanese Unexamined Patent Application Publication No. 2001-348361
Patent document 3: Japanese Unexamined Patent Application Publication No. 2003-342260
Patent document 4: Japanese Unexamined Patent Application Publication No. 2011-83755
Patent document 5: Japanese Unexamined Patent Application Publication No. 2011-68631

SUMMARY OF THE INVENTION

Technical Problem

Accordingly, an object of the invention is to provide a metal complex that can be used as a gas-adsorbent material having a greater amount of adsorption than a conventional gas-adsorbent material, a gas storage material having a greater effective occlusion amount than a conventional gas storage material, or a gas-separating material that ensures superior performance in mixed gas separation compared to a conventional gas-separating material.

Solution to Problem

As a result of intensive study, the present inventors found that the above object can be achieved by a metal complex composed of two kinds of dicarboxylic acid compounds selected from specific dicarboxylic acid compounds, at least one kind of metal ion, and an organic ligand capable of bidentate binding to the metal ion, leading to the completion of the present invention.

Specifically, the present invention provides the following.
(1) A metal complex comprising:
two different dicarboxylic acid compounds (I-1) and (I-2) each of which is selected from a dicarboxylic acid compound (I) represented by the following General Formula (I),

[Formula I]

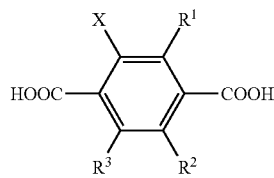

wherein
X is a hydrogen atom, an alkyl group that may have a substituent, an alkoxy group, a formyl group, an acyloxy group, an alkoxycarbonyl group, a nitro group, an amino group, a monoalkyl amino group, a dialkyl amino group, an acylamino group, or a halogen atom, $R^1$, $R^2$, and $R^3$ are the same or different, and each independently represents a hydrogen atom, an alkyl group that may have a substituent, or a halogen atom, and X of the dicarboxylic acid compound (I-1) is an electron-donating group, and X of the dicarboxylic acid compound (I-2) is an electron-withdrawing group;

at least one kind of metal ion selected from metal ions belonging to Group 2 and Groups 7 to 12 of the periodic table; and an organic ligand capable of bidentate binding to the metal ion, wherein the molar ratio of the dicarboxylic acid compound (I-1) to the dicarboxylic acid compound (I-2) is in the range from 20:80 to 99:1.

(2) The metal complex according to item (1), wherein X of the dicarboxylic acid compound (I-1) is an alkyl group that may have a substituent, an alkoxy group or hydrogen atom and X of the dicarboxylic acid compound (I-2) is a formyl group, a nitro group, a fluorine atom, a chlorine atom, a bromine atom, an iodine atom or a hydrogen atom, unless X of the dicarboxylic acid compound (I-1) and X of the dicarboxylic acid compound (I-2) are hydrogen atoms simultaneously.

(3) The metal complex according to item (1) or item (2), wherein the combination of the dicarboxylic acid compound (I-1) and the dicarboxylic acid compound (I-2) is 2-methoxyterephthalic acid and 2-nitroterephthalic acid, 2-methylterephthalic acid and 2-nitroterephthalic acid, 2-methoxyterephthalic acid and terephthalic acid, 2-methylterephthalic acid and terephthalic acid, terephthalic acid and 2-nitroterephthalic acid, terephthalic acid and 2-fluoroterephthalic acid, terephthalic acid and 2-chloroterephthalic acid, terephthalic acid and 2-bromoterephthalic acid, and terephthalic acid and 2-iodoterephthalic acid.

(4) The metal complex according to any one of items (1) to (3), wherein the organic ligand capable of bidentate binding is at least one selected from 4,4'-bipyridyl, 2,2'-dimethyl-4,4'-bipyridine, 1,2-bis(4-pyridyl)ethyne, 1,4-bis(4-pyridyl)butadiyne, 1,4-bis(4-pyridyl)benzene, 3,6-di(4-pyridyl)-1, 2, 4, 5-tetrazine, 2,2'-bi-1,6-naphthyridine, phenazine, diazapyrene, trans-1,2-bis(4-pyridyl)ethene, 4,4'-azopyridine, 1,2-bis(4-pyridyl)ethane, 4,4'-dipyridyl sulfide, 1,3-bis(4-pyridyl)propane, 1,2-bis(4-pyridyl)glycol, N-(4-pyridyl)isonicotinamide, 2,6-di(4-pyridyl)benzo[1,2-c:4,5-c']dipyrrol-1,3,5,7(2H, 6H)-tetrone, 4,4'-bis(4-pyridyl)biphenylene, and N,N'-di(4-pyridyl)-1,4,5,8-naphthalenetetracarboxydiimide.

(5) The metal complex according to any one of items (1) to (4), wherein the metal ion is a copper ion or a zinc ion.

(6) The metal complex according to any one of items (1) to (5), wherein the ratio of the dicarboxylic acid compound (I) to the organic ligand capable of bidentate binding, both forming the metal complex, is 2:1.

(7) An adsorbent material comprising the metal complex according to any one of items (1) to (6).

(8) The adsorbent material according to item (7), wherein the adsorbent material is a adsorbent material for adsorbing carbon dioxide, hydrogen, carbon monoxide, oxygen, nitrogen, hydrocarbon having 1 to 4 carbon atoms, noble gas, hydrogen sulfide, ammonia, sulfur oxide, nitrogen oxide, siloxane, water vapor, or organic vapor.

(9) A storage material comprising the metal complex according to any one of items (1) to (6).

(10) The storage material according to item (9), wherein the storage material is a storage material for storing carbon dioxide, hydrogen, carbon monoxide, oxygen, nitrogen, hydrocarbon having 1 to 4 carbon atoms, noble gas, hydrogen sulfide, ammonia, water vapor, or organic vapor.

(11) A gas storage device comprising a pressure-resistant container and a gas storage space provided inside the pressure-resistant container, wherein the pressure-resistant container can be made airtight and has an outlet and an inlet for a gas, and the storage material according to item (9) is provided in the gas storage space.

(12) A gas-fueled automobile comprising an internal-combustion engine that obtains a driving force from a fuel gas supplied from the gas storage device according to item (11).

(13) A separating material comprising the metal complex according to any one of items (1) to (6).

(14) The separating material according to item (13), wherein the separating material is a separating material for separating carbon dioxide, hydrogen, carbon monoxide, oxygen, nitrogen, hydrocarbon having 1 to 4 carbon atoms, noble gas, hydrogen sulfide, ammonia, sulfur oxide, nitrogen oxide, siloxane, water vapor, or organic vapor.

(15) The separating material according to item (13), wherein the separating material is a separating material for separating methane and carbon dioxide, hydrogen and carbon dioxide, nitrogen and carbon dioxide, ethylene and carbon dioxide, methane and ethane, ethane and ethylene, propane and propene, ethylene and acetylene, nitrogen and methane, or air and methane.

(16) A separation method using the separating material according to item (13) comprising contacting the metal complex and a mixed gas in a pressure range from 0.01 MPa to 10 MPa.

(17) The separation method according to item (16), wherein the separation method is a pressure swing adsorption process or a temperature swing adsorption process.

(18) A method for producing the metal complex according to item (1) comprising reacting, in a solvent, the dicarboxylic acid compound (I), the at least one kind of metal ion selected from metal ions belonging to Group 2 and Groups 7 to 12 of the periodic table, and the organic ligand capable of bidentate binding to the metal ion to precipitate the metal complex.

Advantageous Effects of the Invention

The present invention provides a metal complex comprising two kinds of dicarboxylic acid compounds selected from specific dicarboxylic acid compounds, at least one kind of metal ion, and an organic ligand capable of bidentate binding to the metal ion.

Due to its superior adsorption performance with respect to various gases, the metal complex of the present invention can be used as an adsorbent material for adsorbing hydrogen, carbon monoxide, oxygen, nitrogen, hydrocarbon having 1 to 4 carbon atoms, noble gas, hydrogen sulfide, ammonia, sulfur oxide, nitrogen oxide, siloxane, water vapor, organic vapor, or the like.

Further, due to its superior storage performance with respect to various gases, the metal complex of the present invention can also be used as a storage material for storing carbon dioxide, hydrogen, carbon monoxide, oxygen, nitrogen, hydrocarbon having 1 to 4 carbon atoms, noble gas, hydrogen sulfide, ammonia, water vapor, the organic vapor, or the like.

Furthermore, due to its superior separation performance with respect to various gases, the metal complex of the present invention can further be used as a separating material for separating carbon dioxide, hydrogen, carbon monoxide, oxygen, nitrogen, hydrocarbon having 1 to 4 carbon atoms, noble gas, hydrogen sulfide, ammonia, sulfur oxide, nitrogen oxide, siloxane, water vapor, organic vapor, or the like.

Figure 1:
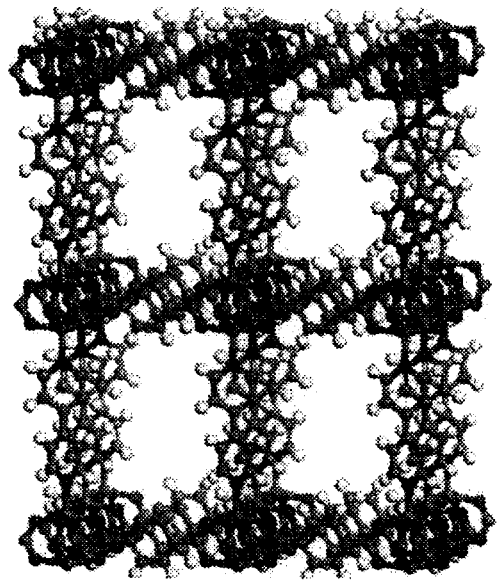
FIG. 1 is a schematic view showing a jungle-gym-type framework in which an organic ligand capable of bidentate binding is coordinated to the axial position of a metal ion in a paddle-wheel-type framework composed of a metal ion and a carboxylate ion of the dicarboxylic acid compound (I).

In the measurement results of a powder X-ray diffraction pattern, the horizontal axis represents a diffraction angle (2θ) and the vertical axis represents a diffraction intensity expressed in cps (counts per second).

In the measurement results of an adsorption/desorption isotherm, the horizontal axis represents an equilibrium pressure expressed in kPa or MPa, and the vertical axis represents an equilibrium adsorption amount expressed in mL(STP)/g. In the measurement results of an adsorption/desorption isotherm, the adsorption amounts (ads.) of the gases (such as carbon dioxide, methane, ethylene, ethane, or nitrogen) under increased pressure and the adsorption amounts (des.) of the gases under decreased pressure are plotted for each pressure level. STP (Standard Temperature and Pressure) denotes a state at a temperature of 273.15 K and a pressure of 1 bar ($10^5$ Pa).

In the measurement result of a breakthrough curve, the horizontal axis represents flow time of gas in minutes (Time [min]) and the vertical axis represents a ratio of an outlet gas (Outlet Gas Ratio [%]).

DESCRIPTION OF EMBODIMENTS

The metal complex of the present invention comprises two kinds of dicarboxylic acid compounds (I) consisting of a dicarboxylic acid compound (I-1) selected from terephthalic acid derivatives having an electron-donating group in the 2nd position and a dicarboxylic acid compound (I-2) selected from terephthalic acid derivatives having an electron-withdrawing group in the 2nd position; at least one kind of metal ion selected from metal ions belonging to Group 2 and Groups 7 to 12 of the periodic table; and an organic ligand capable of bidentate binding to the metal ion.

The dicarboxylic acid compounds (I) and the dicarboxylic acid compounds (II) that are used for the present invention and that are different each other are both represented by the following General Formula (I):

[Formula 2]

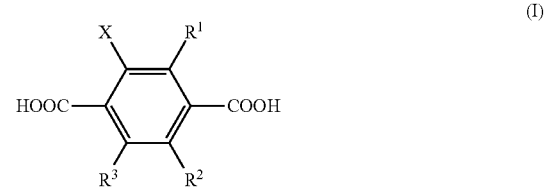

wherein

X is a hydrogen atom, an alkyl group that may have a substituent, an alkoxy group, a formyl group, an acyloxy group, an alkoxycarbonyl group, a nitro group, an amino group, a monoalkyl amino group, a dialkyl amino group, an acylamino group, or a halogen atom. $R^1$, $R^2$, and $R^3$ are the same or different, and each independently represents a hydrogen atom, an alkyl group that may have a substituent, or a halogen atom. X of the dicarboxylic acid compound (I-1) is an electron-donating group, and X of the dicarboxylic acid compound (I-2) is an electron-withdrawing group. X of the dicarboxylic acid compound (I-1) is an electron-donating group selected from the group or the atom as described above. Specifically, an alkyl group that may have a substituent, an alkoxy group, an acyloxy group, an amino group, and the like are included. X of the dicarboxylic acid compound (II-1) is an electron-withdrawing group selected from the group or the atom as described above. Specifically, a formyl group, an alkoxycarbonyl group, a nitro group, an acylamino group, a halogen atom, and the like are included. In this specification, when X of one dicarboxylic acid compound is an electron-donating substituent group and X of the other dicarboxylic acid compound is hydrogen, the hydrogen is defined as an electron-withdrawing group. When X of one dicarboxylic acid compound is an electron-withdrawing substituent group and X of the other dicarboxylic acid compound is hydrogen, the hydrogen is defined as an electron-donating group.

Among the substituents constituting X, the carbon number of the alkyl group or alkoxy group is preferably in a range of 1 to 5. Examples of the alkyl group include linear or branched alkyl groups such as methyl, ethyl, n-propyl, isopropyl, n-butyl, isobutyl, tert-butyl, and pentyl. Examples of the alkoxy group include methoxy, ethoxy, n-propoxy, isopropoxy, n-butoxy, isobutoxy, and tert-butoxy groups. Examples of the acyloxy group include acetoxy, n-propanolyoxy, n-butanoyloxy, pivaloyloxy, and benzoyloxy groups. Examples of the alkoxycarbonyl group include methoxy carbonyl, ethoxy carbonyl, and n-butoxycarbonyl groups. An example of the amino group includes N,N-dimethyl amino group. Examples of a halogen atom include a fluorine atom, chlorine atom, bromine atom, and iodine atom. Further, examples of the substituents that the alkyl group may have include alkoxy groups (such as methoxy, ethoxy, n-propoxy, isopropoxy, n-butoxy, isobutoxy, and tert-butoxy), amino group, formyl group, epoxy group, acyloxy groups (such as acetoxy, h-propanoyloxy, n-butanoyloxy, pivaloyloxy, and benzoyloxy), alkoxycarbonyl groups (such as methoxycarbonyl, ethoxycarbonyl, and n-butoxycarbonyl), and carboxylic anhydride groups (—CO—O—CO—R groups in which R represents an alkyl group having 1 to 5 carbon atoms). The number of the substituents of the alkyl group is preferably from 1 to 3, more preferably 1.

Examples of the alkyl group that may have a substituent which can constitute the above $R^1$, $R^2$, and $R^3$, and a halogen atom are the same as those referred to for the above X.

As the electron-donating substituent or atom that constitutes X of the dicarboxylic acid compound (I-1), an alkyl group that may have a substituent, alkoxy group, or a hydrogen atom is preferred. As the electron-withdrawing substituent or atom that constitutes X of the dicarboxylic acid compound (I-2), a formyl group, a nitro group, a fluorine atom, a chlorine atom, a bromine atom, iodine atoms, or a hydrogen atom is preferred, unless X of the dicarboxylic acid compound (I-1) and X of the dicarboxylic acid compound (I-2) are hydrogen atoms simultaneously.

As a combination of the dicarboxylic acid compound (I-1) and the dicarboxylic acid compound (I-2), preferred are 2-methoxy terephthalic acid and 2-nitroterephthalic acid, 2-methylterephthalic acid and 2-nitroterephthalic acid, 2-methoxyterephthalic acid and terephthalic acid, 2-methylterephthalic acid and terephthalic acid, terephthalic acid and 2-nitroterephthalic acid, terephthalic acid and 2-fluoroterephthalic acid, terephthalic acid and 2-chloroterephthalic acid, terephthalic acid and 2-bromoterephthalic acid, and terephthalic acid and 2-iodoterephthalic acid.

The metal complex used for the present invention includes two kinds of dicarboxylic acid compounds (I-1) and (I-2). Here, the dicarboxylic acid compound (I-1) may include two or more kinds of dicarboxylic acid compounds (I-1) as long as X is an electron-donating group. The dicarboxylic acid compound (I-2) may include two or more kinds of dicarboxylic acid compounds (I-2) as long as X is an electron-withdrawing group.

The mixing ratio of the two kinds of dicarboxylic acid compounds selected from dicarboxylic acid compounds (I) is, by the molar ratio of the dicarboxylic acid compound (I-1) to the dicarboxylic acid compound (I-2) (dicarboxylic acid compound (I-1) : dicarboxylic acid compound (I-2)), within the range of =20:80 to 99:1. Outside this range, the adsorption performance of gas, the occlusion performance of gas, and the separation performance of mixed gas are deteriorated. More preferably, the molar ratio of the dicarboxylic acid compound (I-1) to the dicarboxylic acid compound (I-2) is within the range of 30:70 to 95:5.

When two or more kinds of the dicarboxylic acid compounds (I-1) are contained, the sum of the mole numbers may fall within the above range. Similarly, when two or more kinds of the dicarboxylic acid compounds (I-2) are contained, the sum of the mole numbers may fall within the above range.

The ratio of the dicarboxylic acid compound (I-1) and a dicarboxylic acid compound (I-2) that constitute the metal complex of the invention may be determined by degrading the metal complex into a uniform solution and then analyzing the solution using gas chromatography, high-performance chromatography, or NMR.

As the metal ion belonging to Group 2 and Groups 7 to 12 of the periodic table used for the invention, for example, a magnesium ion, a calcium ion, a manganese ion, a cobalt ion, a nickel ion, a copper ion, a zinc ion, a cadmium ion, and the like may be used. In particular, a copper ion and zinc ion are preferred. For a metal ion, use of one kind of metal ion is preferred, but a mixed metal complex including two or more kinds of metal ions may also be formed. Further, as a metal complex of the invention, two or more metal complexes, each of which includes one kind of metal ion, may be mixed for use.

The metal ion may be used in the form of a metal salt. As a metal salt, for example, a magnesium salt, a calcium salt, a manganese salt, a cobalt salt, a nickel salt, a copper salt, a zinc salt, a cadmium salt, and the like may be used. A copper salt and a zinc salt are particularly preferred. As these metal salts, a salt of an organic acid such as acetate and formate, sulfate, nitrate, carbonate, hydrochloride, and a salt of an inorganic acid such as a salt of hydrobromic acid may be used.

The organic ligand capable of bidentate binding that is used for the present invention means a neutral ligand having two or more positions coordinated to a metal ion with a lone electron pair.

As the positions coordinated to a metal ion with a lone electron pair, a nitrogen atom, an oxygen atom, a phosphorus atom, a sulfur atom, and the like are included. The organic ligand capable of bidentate binding is preferably a heterocyclic compound, in particular, a heterocyclic compound that has a nitrogen atom in the coordination positions. The heterocyclic compound may have a substituent.

As the organic ligand capable of bidentate binding, for example, it is possible to use 4,4'-bipyridyl, 2,2'-dimethyl-4,4'-bipyridine, 1,2-bis(4-pyridyl)ethyne, 1,4-bis(4-pyridyl)butadiyne, 1,4-bis(4-pyridyl)benzene, 3,6-di(4-pyridyl)-1,2,4,5-tetrazine, 2,2'-bi-1,6-naphthyridine), phenazine, 2,7-diazapyrene, trans-1,2-bis(4-pyridyl)ethene, 4,4'-azopyridine, 1,2-bis(4-pyridyl)ethane, 4,4'-dipyridylsulfide, 1,3-bis(4-pyridyl)propane, 1,2-bis(4-pyridyl)glycol, N-(4-pyridyl)isonicotinamide, 2,6-di(4-pyridyl)benzo[1,2-c:4,5-c']dipyrrol-1,3,5,7(2H,6H)-tetrone, 4,4'-bis(4-pyridyl)biphenylene, N,N'-di(4-pyridyl)-1,4,5,8-naphthalene tetracarboxydiimide, and the like. Among these, preferred is the organic ligand that belongs to the $D\infty_h$ point group and has a longitudinal length of not less than 7.0 Å and not more than 16.0 Å, such as 4,4'-bipyridyl, 2,7-diazapyrene, 1,2-bis(4-pyridyl)ethyne, 1,4-bis(4-pyridyl)butadiyne, 1,4-bis(4-pyridyl)benzene, 3,6-di(4-pyridyl)-1,2,4,5-tetrazine, 2,6-di(4-pyridyl)-benzo[1,2-c:4,5-c']dipyrrol-1,3,5,7(2H,6H)-tetrone, 4,4'-bis(4-pyridyl)biphenylene, N,N'-di(4-pyridyl)-1,4,5,8-naphthalene tetracarboxydiimide, and the like.

Particularly preferred is 4,4'-bipyridyl.

The point group to which the organic ligand capable of bidentate binding belongs may be determined according to the method disclosed in Reference Document 1 below.

Reference Document 1: Bunshino Taisho to Gunron (Molecular Symmetry and Group Theory; Masao Nakazaki, 1973, Tokyo Kagaku Dojin Co., Ltd.) pp.39-40.

For example, since 4,4'-bipyridyl, 1,2-bis(4-pyridyl)ethyne, 2,7-diazapyrene, 1,4-bis(4-pyridyl)benzene, 3,6-di(4-pyridyl)-1,2,4,5-tetrazine, 2,6-di(4-pyridyl)-benzo[1,2-c:4,5-c']dipyrrol-1,3,5,7(2H,6H)-tetrone, 4,4'-bis(4-pyridyl)biphenylene and N,N'-di(4-pyridyl)-1,4,5,8-naphthalene tetracarboxydiimide are symmetric linear molecules having a symmetric center, they belong to the $D\infty_h$ point group. Also, since 1,2-bis(4-pyridyl)ethene has a two-fold axis and symmetric planes perpendicular to the axis, it belongs to the $C_{2h}$ point group. Further, since 1,2-bis(4-pyridyl)ethene has a two-fold axis and symmetric planes perpendicular to the axis, it belongs to the $C_{2h}$ point group.

When the point group of the organic ligand capable of bidentate binding is $D\infty_h$, the high symmetry reduces wasteful gaps. Thus, high adsorption performance is exhibited. In addition, when the longitudinal length is not less than 7.0 Å and not more than 16.0 Å, the distance between the metal ions in the metal complex will be suitable. Thus, a metal complex having optimal gaps for adsorbing and desorbing a gas molecule may be formed.

The longitudinal length of the organic ligand capable of bidentate binding of the present specification is defined as the distance between the nitrogen atoms having the longest distance therebetween among the atoms coordinated to the metal ion in the structural formula, in the most stable structure found by structure optimization according to the PM5 semiempirical molecular orbital method after the conformational analysis according to the MM3 molecular dynamics method using Scigress Explorer Professional Version 7.6.0.52 (produced by Fujitsu).

For example, the interatomic distance between nitrogen atoms of 1,4-diazabicyclo[2.2.2]octane is 2.609 Å, the interatomic distance between nitrogen atoms of pyrazine is 2.810 Å, the interatomic distance between nitrogen atoms of 4,4'-bipyridyl is 7.061 Å, the interatomic distance between nitrogen atoms of 1,2-bis(4-pyridyl)ethyne is 9.583 Å, the 1,4-bis(4-pyridyl)benzene interatomic distance between nitrogen atoms is 11.315 Å, the interatomic distance between nitrogen atoms of 3,6-di(4-pyridyl)-1,2,4,5-tetrazine is 11.204 Å, the interatomic distance between nitrogen atoms of 2,6-di(4-pyridyl)-benzo[1,2-c:4,5-c']dipyrrol-1,3,5,7(2H,6H)-tetrone is 15.309 Å, the interatomic distance between nitrogen atoms of 4,4'-bis(4-pyridyl)biphenylene is 15.570 Å, and the interatomic distance between nitrogen atoms of N,N'-di(4-pyridyl)-1,4,5,8-naphthalenetetracarboxydiimide is 15.533 Å.

The metal complex of the present invention may further include a monocarboxylic acid compound other than the above constituents. As the monocarboxylic acid compound, for example, it is possible to use formic acid; aliphatic monocarboxylic acid such as acetic acid, propionic acid, butyric acid, isobutyric acid, valeric acid, caproic acid, enanthic acid, cyclohexane carboxylic acid, caprylic acid, octylic acid, pelargonic acid, capric acid, lauric acid, myristic acid, pentadecyl acid, palmitic acid, margaric acid, stearic acid, tuberculostearic acid, arachidic acid, behenic acid, lignoceric acid, alpha-linoleic acid, eicosapentaenoic acid, docosahexaenoic acid, linolic acid, and oleic acid; aromatic monocarboxylic acid such as benzoic acid; complex aromatic monocarboxylic acid such as nicotinic acid and isonicotinic acid; and the like. Among these, formic acid, acetic acid, octylic acid, lauric acid, myristic acid, palmitic acid, and stearic acid are preferred.

The monocarboxylic acid compound may be used in the form of acid anhydride or alkali metal salt, and may be used as a counteranion of the metal start of the starting material. The monocarboxylic acid compound may be present from the early stage of the reaction, or may be added in the latter stage of the reaction.

When the metal complex of the invention includes the monocarboxylic acid compound, the ratio thereof is not particularly limited unless it impairs the effect of the invention. However, the composition ratio of the multivalent carboxylic acid compound to the monocarboxylic acid compound is preferably within the range from 100:1 to 5,000:1, and more preferably, within the range from 250:1 to 2,500:1. The composition ratio can be determined by analyzing using gas chromatography, high-performance chromatography, or NMR.

The metal complex of the invention may further include a monodentate organic ligand unless it impairs the effect of the invention. The monodentate organic ligand means a neutral ligand having one position coordinated to a metal ion with a lone electron pair. As a monodentate organic ligand, for example, furan, thiophene, pyridine, quinoline, isoquinoline, acridine, triphenyl phosphine, triphenyl phosphite, a methylisocyanide, and the like may be used. Pyridine is particularly preferred. The monodentate organic ligand may have a hydrocarbon group having a number of carbon atoms of 1 to 23 as a substituent.

When the metal complex of the invention includes the monodentate organic ligand, the ratio thereof is not particularly limited unless it impairs the effect of the invention. However, the composition ratio of the organic ligand capable of bidentate binding to the monodentate organic ligand is preferably within the range from the molar ratio of 1:5 to 1:1,000, and more preferably, within the range from 1:10 to 1:100. The composition ratio can be determined by analyzing using gas chromatography, high-performance chromatography, or NMR.

The metal complex of the invention may be produced by reacting two different kinds of dicarboxylic acid compounds (I-1) and (I-2) selected from the dicarboxylic acid compound (I), at least one kind of metal salt selected from metal salts belonging to Group 2 and Groups 7 to 12 of the periodic table, and the organic ligand capable of bidentate binding to the metal salt in either a vapor phase, a liquid phase, or a solid phase. It is preferred to produce the metal complex by reacting in a solvent for several hours to several days under ordinary pressure to perform precipitation. For example, the metal complex can be obtained by mixing an aqueous solution or an organic solvent solution of the metal salt and an aqueous solution or an organic solvent solution containing two kinds of dicarboxylic acid compounds selected from the dicarboxylic acid compound (I) and the organic ligand capable of bidentate binding under ordinary pressure to react.

The mixing ratio of the dicarboxylic acid compound (I) [the sum of mole number of the dicarboxylic acid compound (I-1) and mole number of the dicarboxylic acid compound (I-2)] to the organic ligand capable of bidentate binding during the manufacture of the metal complex (the dicarboxylic acid compound (I): the organic ligand capable of bidentate binding) is preferably within the range of molar ratio from 1:5 to 8:1, more preferably within the range molar ratio from 1:3 to 6:1. If the mixing ratio falls out of this range during the reaction, the yield decreases and side reaction increases, even though the target metal complex can be obtained.

The mixing ratio of the metal salt to the organic ligand capable of bidentate binding during the manufacture of the metal complex preferably falls in the following molar ratio: metal salt:organic ligand capable of bidentate binding=3:1 to 1:3, more preferably 2:1 to 1:2. If the mixing ratio falls out of this range during the reaction, the yield of metal complex decreases and residues of unreacted material are generated, thereby causing complication in the purification process of the resulting metal complex.

The molar concentration of the dicarboxylic acid compound (I) [the sum of molar concentrations of the dicarboxylic acid compound (I-1) and the dicarboxylic acid compound (I-2)] in the solvent used for the manufacture of the metal complex is preferably 0.005 to 5.0 mol/L, more preferably 0.01 to 2.0 mol/L. If the molar concentration falls below this range upon the reaction, the yield of reaction undesirably decreases even though the target metal complex can still be obtained. If the molar concentration falls above this range upon the reaction, the solubility decreases, thereby hindering the progress of reaction.

The molar concentration of the metal salt in the solvent used for the manufacture of the metal complex is preferably 0.005 to 5.0 mol/L, more preferably 0.01 to 2.0 mol/L. If the molar concentration falls below this range upon the reaction, the yield of reaction undesirably decreases even though the target metal complex can still be obtained. If the molar concentration falls above this range, residues of unreacted metal salts are generated, thereby causing complication in the purification process of the resulting metal complex.

The molar concentration of the organic ligand capable of bidentate binding in the solvent used for the manufacture of the metal complex is preferably 0.001 to 5.0 mol/L, more preferably 0.005 to 2.0 mol/L. If the molar concentration falls below this range upon the reaction, the yield of reaction undesirably decreases even though the target metal complex can still be obtained. If the molar concentration falls above this range upon the reaction, the solubility decreases, thereby hindering the progress of reaction.

The solvent used for the manufacture of a metal complex may be an organic solvent, water, or a mixed solvent of these.

Specific examples of the solvents include methanol, ethanol, propanol, diethyl ether, dimethoxyethane, tetrahydrofuran, hexane, cyclohexane, heptane, benzene, toluene, methylene chloride, chloroform, acetone, acetic acidethyl, acetonitrile, N,N-dimethylformamide, water, or mixed solvents of these substances. The reaction temperature preferably falls in a range of 253 to 423 K.

The completion of the reaction may be confirmed by analyzing the remaining amount of the raw materials by using gas chromatography or high-performance liquid chromatography. After the reaction is completed, the resulting mixture is subjected to suction filtration to collect the precipitates. The precipitates are washed with an organic solvent and dried in vacuum for several hours at about 373 K, thereby yielding the metal complex of the present invention.

Figure 2:
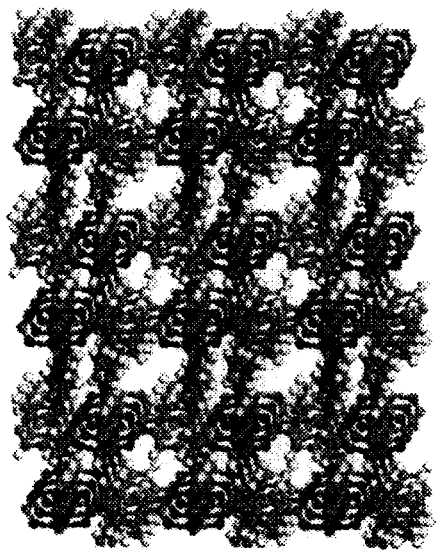
FIG. 2 is a schematic view showing a three-dimensional structure in which two jungle-gym-type frameworks are interpenetrated into each other.

The metal complex of the present invention thus obtained has a three-dimensional structure composed of interpenetrated multiple jungle-gym-type frameworks. The jungle-gym-type framework is structured such that an organic ligand capable of bidentate binding is coordinated to the axial position of a metal ion in a paddle-wheel-type framework composed of a metal ion and a carboxylate ion of the dicarboxylic acid compound (I). FIG. 1 is a schematic diagram showing a jungle-gym-type framework, and FIG. 2 is a schematic diagram showing a three-dimensional structure in which two jungle-gym-type frameworks are interpenetrated into each other.

In the specification, "jungle-gym-type framework" is defined as a jungle-gym-like three-dimensional structure in which an organic ligand capable of bidentate binding is coordinated to the axial position of a metal ion in a framework composed of a carboxylate ion of the dicarboxylic acid compound (I) and a metal ion, thus connecting the two-dimensional lattice sheets composed of the dicarboxylic acid compound (I) and the metal ion.

In the specification, "a structure in which multiple jungle-gym-type frameworks are interpenetrated into each other" is defined as a three-dimensional framework in which a plurality of jungle-gym-type frameworks are interpenetrated into each other by filling each other's micropores.

Whether the metal complex has the aforementioned structure in which multiple jungle-gym-type frameworks are interpenetrated into each other can be confirmed, for example, by single-crystal X-ray crystal structure analysis or powder X-ray crystal structure analysis.

The metal complex of the invention that has a structure in which multiple jungle-gym-type frameworks are interpenetrated into each other includes the dicarboxylic acid compound (I) (the sum of the dicarboxylic acid compound (I-1) and the dicarboxylic acid compound (I-2)): the metal ion: the organic ligand capable of bidentate binding=2:2:1 (molar ratio). The molar ratio of each element forming the metal complex can be confirmed by single-crystal X-ray crystal structure analysis, powder X-ray crystal structure analysis, elemental analysis, and the like. That is, the molar ratio of the dicarboxylic acid compound (I) to the organic ligand capable of bidentate binding is as follows: the dicarboxylic acid compound (I) (the sum of the dicarboxylic acid compound (I-1) and the dicarboxylic acid compound (I-2)): the organic ligand capable of bidentate binding=2:1. The molar ratio of the dicarboxylic acid compound (I) to the organic ligand capable of bidentate binding may be analyzed not only by single-crystal X-ray crystal structure analysis, powder X-ray crystal structure analysis, or elemental analysis, but also by gas chromatography, high-performance liquid chromatography, or NMR.

Figure 3:
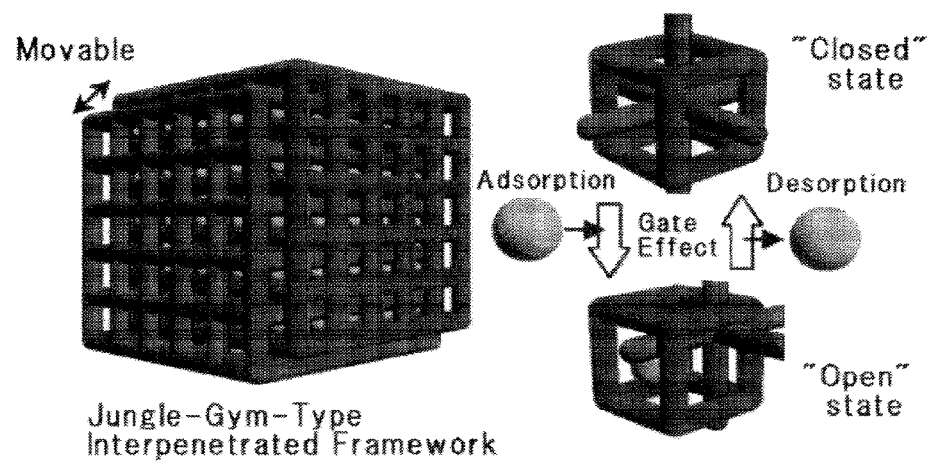
FIG. 3 is a schematic view showing structural change of the metal complex of the present invention upon adsorption and desorption.

The three-dimensional structure of the metal complex of the invention can also change in crystal form after synthesis, and so with this change, the structure or the size of pores also changes. Conditions causing this structural change depend on the kind of substance to be adsorbed, adsorption pressure, and adsorption temperature. This means that the degree of the structural change differs according to the substance to be adsorbed as well as the difference in the interaction between the pore surface and the substance (the intensity of the interaction being in proportion to the magnitude of the Lennard-Jones potential of the substance), which leads to a high gas adsorption performance, a high gas storage performance, and a high selectivity. FIG. 3 shows a schematic diagram showing structural change upon adsorption and desorption. In the present invention, by using a mixture of dicarboxylic acid compounds forming the metal complex that exhibit a different behavior when each of the dicarboxylic acid compounds is used alone, the features of both dicarboxylic acid compounds are provided. For example, by using a mixture of a dicarboxylic acid compound that has a lower separation ability of a mixed gas but has greater adsorption of a gas to be adsorbed and removed when the partial pressure of the gas is low, together with a dicarboxylic acid compound that has a higher separation ability of a mixed gas but that has less adsorption of a gas to be adsorbed and removed when the partial pressure of the gas is low, both high separation ability of a mixed gas and large adsorption are obtained. In other words, controlling the interacting strength between the pore surface and the gas molecule by using the two kinds of dicarboxylic acid compounds selected from the dicarboxylic acid compounds represented by General Formula (I) achieves high gas adsorption performance, high gas storage performance, and high selectivity. After desorption of the adsorbed substance, the structure of the metal complex returns to the original structure, and so the size of the pores also returns to the original size.

The above selective adsorption mechanism is estimated. Even if an adsorption mechanism does not conform to the above mechanism, it will be covered within the technical scope of the invention insofar as it satisfies the requirements specified in the invention.

Owing to its excellent adsorption performance with respect to various gases, the metal complex of the present invention is useful as an adsorbent. material for adsorbing carbon dioxide, hydrogen, carbon monoxide, oxygen, nitrogen, hydrocarbons having from 1 to 4 carbon atoms (such as methane, ethane, ethylene, acetylene, propane, propene, methylacetylene, propadiene, 1-butene, isobutene and butadiene), noble gases (such as helium, neon, argon, krypton, or xenon), hydrogen sulfide, ammonia, sulfur oxides, nitrogen oxides, siloxanes (such as hexamethylcyclotrisiloxane or octamethylcyclotetrasiloxane), water vapor, or organic vapor.

The term "organic vapor" means a vaporizing gas of an organic substance that is in liquid form at ordinary temperature under ordinary pressure. Examples of such an organic substance include alcohols such as methanol and ethanol, amines such as trimethylamine, aldehydes such as acetaldehyde, aliphatic hydrocarbons having from 5 to 16 carbon atoms, aromatic hydrocarbons such as benzene and toluene, ketones such as acetone and methyl ethyl ketone, and halogenated hydrocarbons such as methyl chloride and chloroform.

Owing to its excellent storing performance with respect to various gases, the metal complex of the present invention is useful for a storage method for storing carbon dioxide, hydrogen, carbon monoxide, oxygen, nitrogen, hydrocarbons having from 1 to 4 carbon atoms (such as methane, ethane, ethylene, acetylene, propane, propene, methylacetylene, propadiene, 1-butene, isobutene and butadiene), noble gases (such as helium, neon, argon, krypton, or xenon), hydrogen sulfide, ammonia, sulfur oxides, nitrogen oxides, siloxanes (such as hexamethylcyclotrisiloxane or octamethylcyclotetrasiloxane), water vapor, and organic vapor. The term "organic vapor" means a vaporizing gas of an organic substance that is in liquid form at ordinary temperature under ordinary pressure. Examples of such an organic substance include alcohols such as methanol and ethanol, amines such as trimethylamine, aldehydes such as acetaldehyde, aliphatic hydrocarbons having from 5 to 16 carbon atoms, aromatic hydrocarbons such as benzene and toluene, ketones such as acetone and methyl ethyl ketone, and halogenated hydrocarbons such as methyl chloride and chloroform.

By utilizing its storage performance, the metal complex of the present invention can also be used for a gas storage device. An example of a gas storage device is a gas storage device comprising a pressure-resistant container and a gas storage space provided inside the pressure-resistant container, wherein the pressure-resistant container can be made airtight and has an outlet and an inlet for a gas, and the storage material comprising the metal complex of the invention is provided in the gas storage space. By injecting a desired gas into the gas storage device, the gas can be adsorbed and stored in the storage material. When the gas is removed from the gas storage device, a pressure valve is opened to decrease the internal pressure in the pressure-resistant container, thereby desorbing the gas. In equipping the gas storage space with the storage material, in terms of handling, the metal complex of the invention may be used in the form of a molded pellet, although the metal complex of the invention may be provided in the form of powder.

Figure 4:
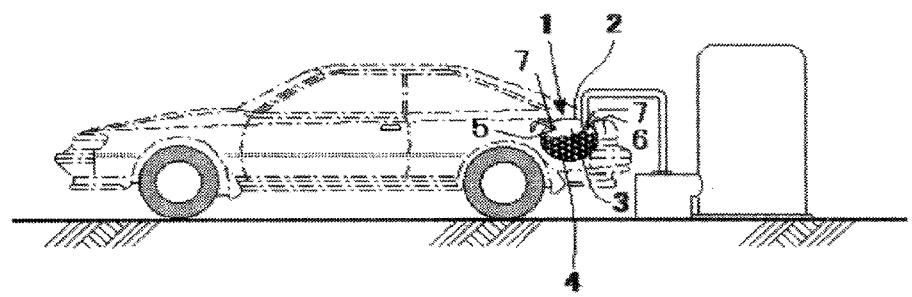
FIG. 4 is an overview of a gas-fueled automobile including a gas storage device.

FIG. 4 shows an example of a gas-fueled automobile including a gas storage device as described above. The gas storage device can store a fuel gas in a gas storage space 3. The gas storage device can be advantageously used as a fuel tank 1 of the gas-fueled automobile. The gas-fueled automobile includes the above gas storage device as a fuel tank 1 and an engine as an internal-combustion engine that obtains natural gas stored in the fuel tank 1 from the fuel tank 1, mixes the natural gas with oxygen-containing gas for combustion (e.g., air) and obtains a driving force from the combustion. The fuel tank 1 includes a pressure-resistant container 2 and both an outlet port 5 and an inlet port 6, which serve as an outlet and an inlet allowing the stored gas to exit and enter the pressure-resistant container 2. A pair of valves 7 are provided at the outlet and inlet and constitute an airtight mechanism that can maintain the gas in the container 2 in a pressurized state. The natural gas as a fuel is put into the fuel tank 1 in a pressurized state at a gas station. A storage material 4 comprising a metal complex of the invention is provided in the fuel tank 1. The storage material 4 adsorbs the natural gas (e.g., gas including methane as a main element) at ordinary temperature in a pressurized state. When the valve 7 at the outlet is opened, the adsorbed gas is desorbed from the storage material 4 and sent to the engine for combustion so that the driving force can be obtained.

Since the fuel tank 1 includes the metal complex of the invention, gas compressibility is higher than the apparent pressure, compared to fuel tanks that do not include a storage material. Thus, the thickness of the tank can be decreased and the gas storage device can be made light-weight as a whole, which is useful for gas-fueled automobiles. In addition, the fuel tank 1 is normally in an ordinary temperature and not particularly cooled. For example, in summer when atmospheric temperature rises, the temperature of the fuel tank 1 becomes relatively high. Even in such a hot temperature range (about 298-333K), the storage material of the invention is useful in that it can hold high adsorption capacity.

Owing to its separation performance with respect to various gases, the metal complex of the present invention is useful for a separation method for separating carbon dioxide, hydrogen, carbon monoxide, oxygen, nitrogen, hydrocarbons having from 1 to 4 carbon atoms (such as methane, ethane, ethylene, acetylene, propane, propene, methylacetylene, propadiene, 1-butene, isobutene and butadiene), noble gases (such as helium, neon, argon, krypton, or xenon), hydrogen sulfide, ammonia, sulfur .oxides, nitrogen oxides, siloxanes (such as hexamethylcyclotrisiloxane or octamethylcyclotetrasiloxane), water vapor, and organic vapor. In particular, the metal complex of the present invention is suitable for separating carbon dioxide in methane, carbon dioxide in hydrogen, carbon dioxide in nitrogen, carbon dioxide in ethylene, ethane in methane, ethane in ethylene, acetylene in ethylene, propene in propane, nitrogen in methane, or methane in air by using a pressure swing adsorption process or a temperature swing adsorption method. The term "organic vapor" means a vaporizing gas of an organic substance that is in liquid form at ordinary temperature under ordinary pressure. Examples of such an organic substance include alcohols such as methanol and ethanol, amines such as trimethylamine, aldehydes such as acetaldehyde, aliphatic hydrocarbons having from 5 to 16 carbon atoms, aromatic hydrocarbons such as benzene and toluene, ketones such as acetone and methyl ethyl ketone, and halogenated hydrocarbons such as methyl chloride and chloroform.

The separation method comprises a step of bringing in contact with each other a gas and the metal complex of the present invention under the condition that enables the gas to be adsorbed to the metal complex. The condition, i.e., the adsorption pressure and the adsorption temperature that enable the gas to be adsorbed to the metal complex can be suitably set according to the type of the material to be adsorbed. For example, the adsorption pressure is preferably 0.01 to 10 MPa, more preferably 0.1 to 3.5 MPa. The adsorption temperature is preferably 195 to 343 K, more preferably 273 to 313 K.

A separation method can be a pressure swing adsorption process or a temperature swing adsorption process. When a separation method is a pressure swing adsorption method, the separation method further includes a step of increasing the pressure from adsorption pressure to the pressure enabling gas to be desorbed from a metal complex. The desorption pressure can be suitably set up according to the kind of substance adsorbed. For example, the desorption pressure is preferably 0.005 to 2 MPa, and more preferably 0.01 to 0.1 MPa. When a separation method is a temperature swing adsorption process, the separation method further includes a step of increasing the temperature from an adsorption temperature to a temperature enabling the gas to be desorbed from the metal complex. The desorption temperature can be suitably set according to the type of the material to be adsorbed. For example, the desorption temperature is preferably 303 to 473 K, and more preferably 313 to 373 K.

When the separation method is the pressure swing adsorption process or the temperature swing adsorption process, the step of bringing the gas in contact with the metal complex and the step of changing the pressure or the temperature that enables the gas to be desorbed from the metal complex may be appropriately repeated.

EXAMPLES

The invention will hereinafter be described specifically by using examples. The invention, however, is not limited to or limited by these examples. The analysis and evaluation in the following Examples and Comparative Examples were conducted as described below.
(1) Measurement of Powder X-ray Diffraction Pattern Using an X-ray diffractometer, the range of diffraction angle (2 theta) from 5 degree to 50 degree was scanned at the scanning speed of 1 degree per minute and measured using the symmetrical reflection method. The details of the analysis conditions are described below.
Analysis Conditions
Apparatus: RINT 2400, Rigaku Corporation
X-ray Source: CuKα (λ=1.5418 Å) 40 kV 200 mA
Goniometer: Vertical Goniometer
Detector: Scintillation Counter
Step Width: 0.02°
Slit: Divergent Slit=0.5°
Receiving Slit=0.15 mm
Scattering Slit=0.5°0
(2) Determination of the Molar Ratio of the Dicarboxylic Acid Compound (I) and the Molar Ratio of the Dicarboxylic Acid Compound (I) to the Organic Ligand Capable of Bidentate Binding A metal complex is dissolved in a mixed solvent of aqueous ammonium and heavy water at weight ratio of 2 to 3 to form a uniform solution. $^1$H NMR measurement was performed on the solution and the molar ratios were calculated from the integration ratio of the spectrum obtained. The details of analysis conditions are described below.
Analysis Conditions
Apparatus: JNM-LA500, JEOL Ltd.
Resonance Frequency: 500 MHz
Solvent: Heavy Water
Temperature: 298 K
Pulse Repetition Period: 7.0 seconds
Integration Count: 16 times
(3) Creation of Adsorption Isotherm or Desorption Isotherm An adsorption/desorption isotherm was measured based on the volumetric method (based on JIS Z8831-2) by using a gas adsorption measuring instrument. Prior to the measurement, the sample was dried at 373 K and 50 Pa for 5 hours to remove adsorbed water and the like. The details of the analysis conditions are described below.
Analysis Conditions
Apparatus: BELSORP-HP, Bel Japan, Inc.
Equilibrium Waiting Time: 500 seconds
(4) Measurement of Breakthrough Curve A pressure-resistant glass container with a volume of 10 mL connected with a cylinder via a stainless steel tube equipped with a gas flowmeter and valves was prepared. The measurement was conducted by placing a sample into the pressure-resistant glass container, drying the sample at 373 K and 7 Pa for 3 hours to remove the adsorbed water or the like, and passing a mixed gas through the container. In this, outlet gas was sampled every 2 minutes and analyzed by gas chromatography to calculate the composition of the outlet gas (the composition of inlet gas was measured beforehand by gas chromatography. The details of analysis conditions are described below.
Analysis Conditions
Apparatus: GC-14B, Shimadzu Corporation
Column: Unibeads C 60/80, GL Sciences, Inc.
Column Temperature: 200° C.
Carrier Gas: Helium
Injection Rate: 1.0 mL
Detector: TCD Synthesis Example 1

Figure 5:
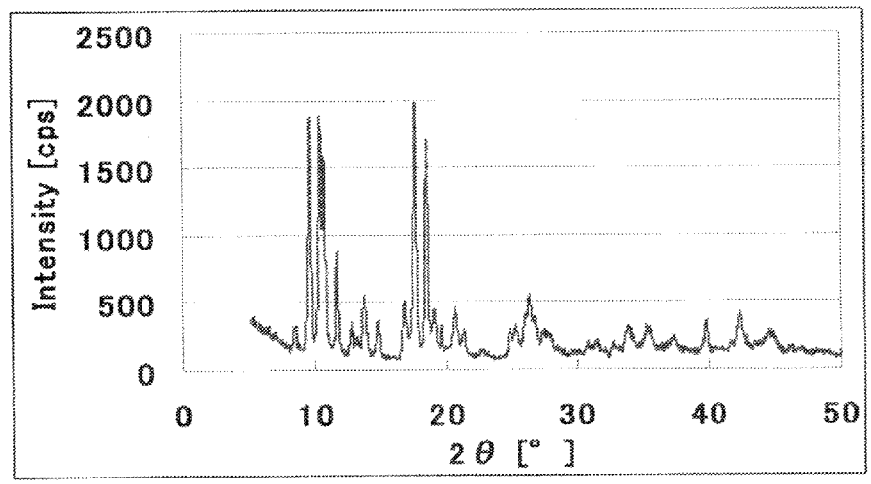
FIG. 5 is a powder X-ray diffraction pattern of the metal complex obtained in Synthesis Example 1.

Under nitrogen atmosphere, 12.6 g (42 mmol) of zinc nitrate hexahydrate, 2.11 g (13 mmol) of terephthalic acid, 6.24 g (30 mmol) of 2-nitroterephthalic acid, and 3.30 g (21 mmol) of 4,4'-bipyridyl were dissolved in 500 mL of a mixed solvent containing N,N-dimethylformamide and ethanol at a volume ratio of 1:1, and the mixture was stirred at 363 K for 24 hours. The precipitated metal complex was recovered by suction filtration and washed three times with methanol. Then, the product was dried at 373 K and 50 Pa for 8 hours to obtain 13.6 g of an intended metal complex (95% of yield). FIG. 5 shows a powder X-ray diffraction pattern of the resulting metal complex.

19.7 mg of the resulting metal complexes were dissolved in 1.25 g of a mixed solvent of aqueous ammonia and heavy water, and $^1$H NMR measurement was performed. As a result of analyzing a spectrum, the molar ratio of terephthalic acid to 2-nitroterephthalic acid (terephthalic acid:2-nitroterephthalic acid) contained in a metal complex was found to be 33:67. It was also found that the ratio of the sum of the molar number of terephthalic acid and the molar number of 2-nitroterephthalic acid to the molar number of 4,4'-bipyridyl contained in the metal complex ([terephthalic acid plus 2-nitroterephthalic acid]:4,4'-bipyridyl) was 2:1.

Synthesis Example 2

Figure 6:
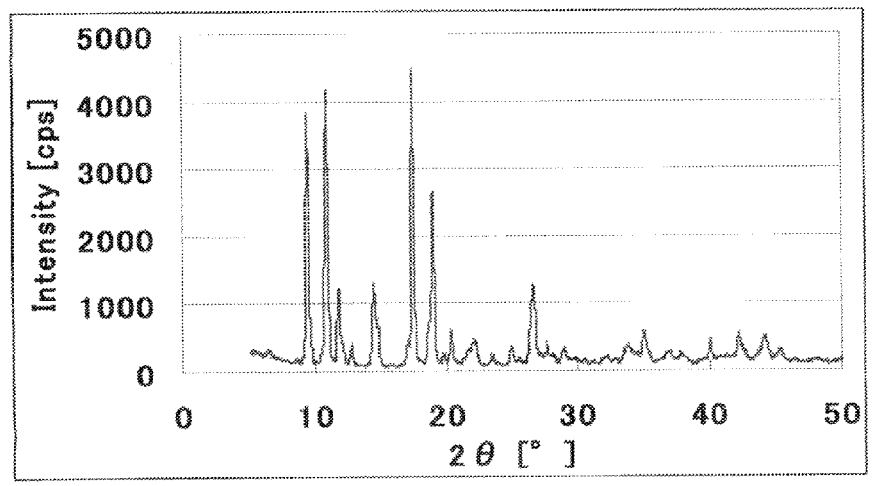
FIG. 6 is a powder X-ray diffraction pattern of the metal complex obtained in Synthesis Example 2.

Under nitrogen atmosphere, 12.6 g (42 mmol) of zinc nitrate hexahydrate, 6.32 g (38 mmol) of terephthalic acid, 0.892 g (4.2 mmol) of 2-nitroterephthalic acid, and 3.30 g (21 mmol) of 4,4'-bipyridyl were dissolved in 500 mL of a mixed solvent containing N,N-dimethylformamide and ethanol at a volume ratio of 1:1, and the mixture was stirred at 363 K for 24 hours. The precipitated metal complex was recovered by suction filtration and washed three times with methanol. Then, the product was dried at 373 K and 50 Pa for 8 hours to obtain 12.5 g of an intended metal complex (94% of yield). FIG. 6 shows a powder X-ray diffraction pattern of the resulting metal complex.

19.8 mg of the resulting metal complexes were dissolved in 1.25 g of a mixed solvent of aqueous ammonia and heavy water, and $^1$H NMR measurement was performed. As a result of analyzing a spectrum, the molar ratio of terephthalic acid to 2-nitroterephthalic acid (terephthalic acid:2-nitroterephthalic acid) contained in a metal complex was found to be 89:11. It was also found that the ratio of the sum of the molar number of terephthalic acid and the molar number of 2-nitroterephthalic acid to the molar number of 4,4'-bipyridyl contained in the metal complex ([terephthalic acid plus 2-nitroterephthalic acid]:4,4'-bipyridyl) was 2:1.

Synthesis Example 3

Figure 7:
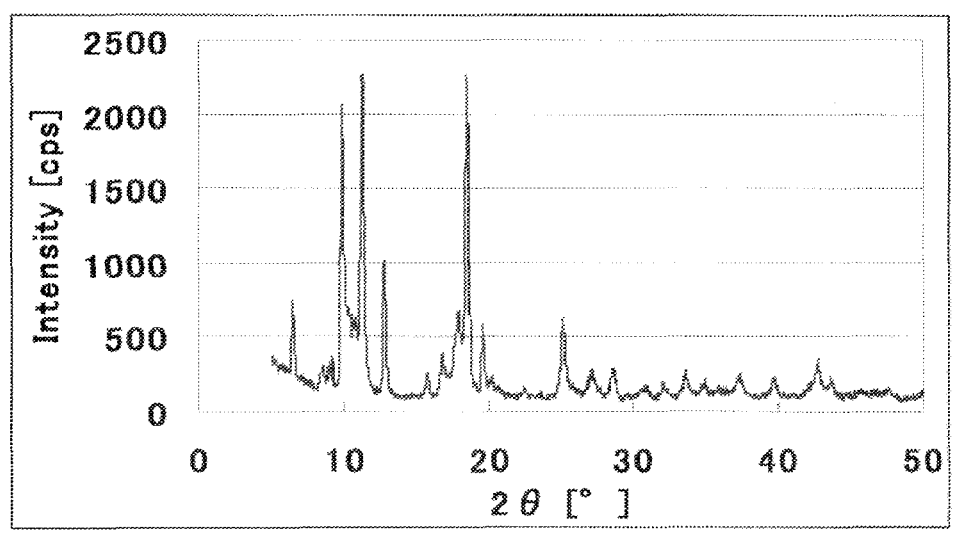
FIG. 7 is a powder X-ray diffraction pattern of the metal complex obtained in Synthesis Example 3.

Under nitrogen atmosphere, 1.26 g (4.2 mmol) of zinc nitrate hexahydrate, 0.381 g (2.1 mmol) of 2-methylterephthalic acid, 0.446 g (2.1 mmol) of 2-nitroterephthalic acid, and 0.331 g (2.1 mmol) of 4,4'-bipyridyl were dissolved in 50 mL of a mixed solvent containing N,N-dimethylformamide and ethanol at a volume ratio of 1:1, and the mixture was stirred at 363 K for 24 hours. The precipitated metal complex was recovered by suction filtration and washed three times with methanol. Then, the product was dried at 373 K and 50 Pa for 8 hours to obtain 1.20 g of an intended metal complex (84% of yield). FIG. 7 shows a powder X-ray diffraction pattern of the resulting metal complex.

20.3 mg of the resulting metal complexes were dissolved in 1.25 g of a mixed solvent of aqueous ammonia and heavy water, and $^1$H NMR measurement was performed. As a result of analyzing a spectrum, the molar ratio of the 2-methylterephthalic acid to 2-nitroterephthalic acid (2-methylterephthalic acid:2-nitroterephthalic acid) contained in a metal complex was found to be 50:50. It was also found that the ratio of the sum of the molar number of 2-methylterephthalic acid and the molar number of 2-nitroterephthalic acid to the molar number of 4,4'-bipyridyl contained in the metal complex ([2-methylterephthalic acid plus 2-nitroterephthalic acid]:4,4'-bipyridyl) was 2:1.

Synthesis Example 4

Under nitrogen atmosphere, 2.51 g (8.5 mmol) of zinc nitrate hexahydrate, 0.70 g (4.2 mmol) of terephthalic acid, 0.893 g (4.2 mmol) of 2-nitroterephthalic acid, and 0.661 g (4.2 mmol) of 4,4'-bipyridyl were dissolved in 100 mL of a mixed solvent containing N,N-dimethylformamide and ethanol at a volume ratio of 1:1, and the mixture was stirred at 363 K for 24 hours. The precipitated metal complex was recovered by suction filtration and washed three times with methanol. Then, the product was dried at 373 K and 50 Pa for 8 hours to obtain 2.55 g of an intended metal complex (91% of yield). FIG. 7 shows a powder X-ray diffraction pattern of the resulting metal complex.

19.6 mg of the resulting metal complexes were dissolved in 1.25 g of a mixed solvent of aqueous ammonia and heavy water, and $^1$H NMR measurement was performed. As a result of analyzing a spectrum, the molar ratio of terephthalic acid to 2-nitroterephthalic acid (terephthalic acid:2-nitroterephthalic acid) contained in a metal complex was found to be 50:50. It was also found that the ratio of the sum of the molar number of terephthalic acid and the molar number of 2-nitroterephthalic acid to the molar number of 4,4'-bipyridyl contained in the metal complex ([terephthalic acid plus 2-nitroterephthalic acid]:4,4'-bipyridyl) was 2:1.

Synthesis Example 5

Figure 9:
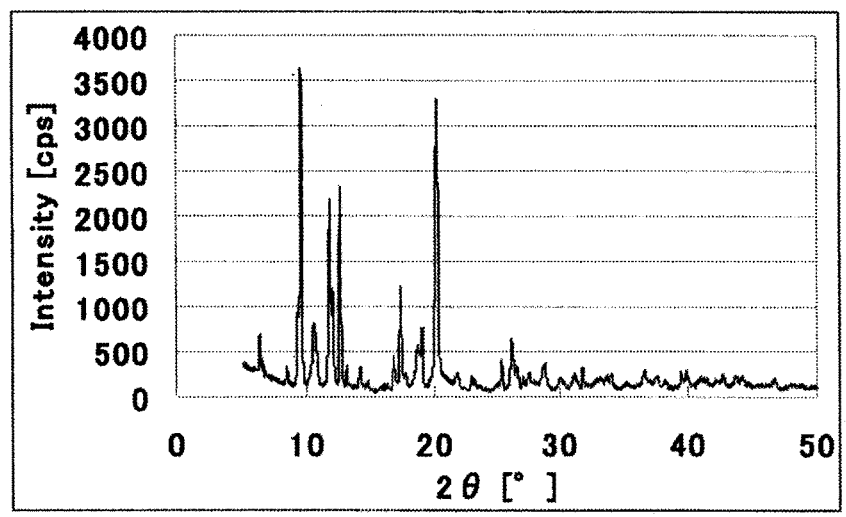
FIG. 9 is a powder X-ray diffraction pattern of the metal complex obtained in Synthesis Example 5.

Under nitrogen atmosphere, 12.6 g (42 mmol) of zinc nitrate hexahydrate, 4.91 g (30 mmol) of terephthalic acid, 2.68 g (13 mmol) of 2-nitroterephthalic acid, and 3.30 g (21 mmol) of 4,4'-bipyridyl were dissolved in 500 mL of a mixed solvent containing N,N-dimethylformamide and ethanol at a volume ratio of 1:1, and the mixture was stirred at 363 K for 24 hours. The precipitated metal complex was recovered by suction filtration and washed three times with methanol. Then, the product was dried at 373 K and 50 Pa for 8 hours to obtain 12.9 g of an intended metal complex (95% of yield). FIG. 9 shows a powder X-ray diffraction pattern of the resulting metal complex.

20.6 mg of the resulting metal complexes were dissolved in 1.25 g of a mixed solvent of aqueous ammonia and heavy water, and $^1$H NMR measurement was performed. As a result of analyzing a spectrum, the molar ratio of terephthalic acid to 2-nitroterephthalic acid (terephthalic acid:2-nitroterephthalic acid) contained in a metal complex was found to be 70:30. It was also found that the ratio of the sum of the molar number of terephthalic acid and the molar number of 2-nitroterephthalic acid to the molar number of 4,4'-bipyridyl contained in the metal complex ([terephthalic acid plus 2-nitroterephthalic acid]:4,4'-bipyridyl) was 2:1.

Synthesis Example 5

Figure 10:
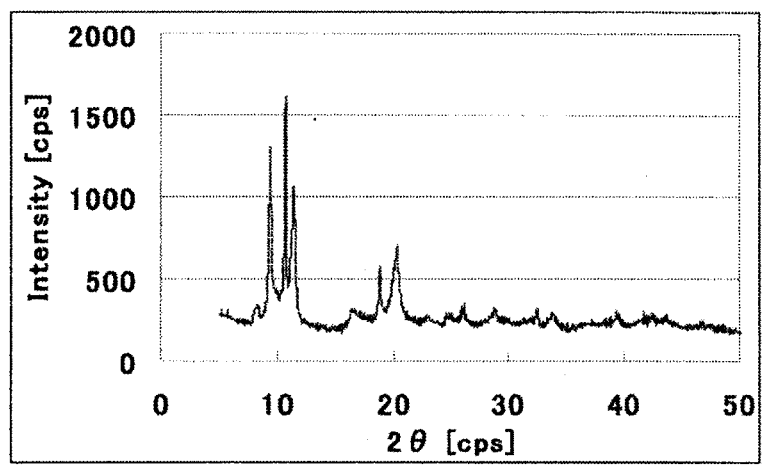
FIG. 10 is a powder X-ray diffraction pattern of the metal complex obtained in Synthesis Example 6.

Under nitrogen atmosphere, 1.61 g (5.4 mmol) of zinc nitrate hexahydrate, 0.26 g (1.6 mmol) of terephthalic acid, 0.798 g (3.8 mmol) of 2-nitroterephthalic acid, and 0.487 g (2.7 mmol) of 1,2-bis(4-pyridyl)ethyne were dissolved in 64 mL of a mixed solvent containing N,N-dimethylformamide and ethanol at a volume ratio of 1:1, and the mixture was stirred at 363 K for 24 hours. The precipitated metal complex was recovered by suction filtration and washed three times with methanol. Then, the product was dried at 373 K and 50 Pa for 8 hours to obtain 1.51 g of an intended metal complex (79% of yield). FIG. 10 shows a powder X-ray diffraction pattern of the resulting metal complex.

19.2 mg of the resulting metal complexes were dissolved in 1.25 g of a mixed solvent, of aqueous ammonia and heavy water, and $^1$H NMR measurement was performed. As a result of analyzing a spectrum, the molar ratio of terephthalic acid to 2-nitroterephthalic acid (terephthalic acid:2-nitroterephthalic acid) contained in a metal complex was found to be 30:70. It was also found that the ratio of the sum of the molar number of terephthalic acid and the molar number of 2-nitroterephthalic acid to the molar number of 1,2-bis(4-pyridyl)ethyne contained in the metal complex ([terephthalic acid plus 2-nitroterephthalic acid]: 1,2-bis(4-pyridyl)ethyne) was 2:1.

Comparative Synthesis Example 1

Figure 11:
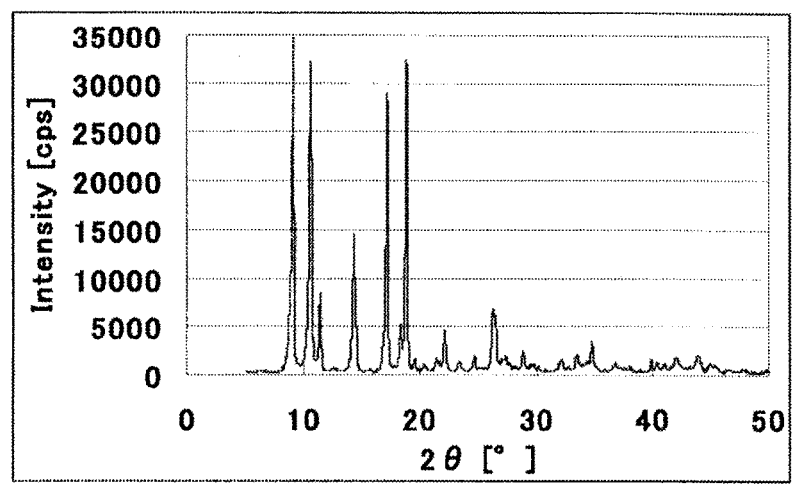
FIG. 11 is a powder X-ray diffraction pattern of the metal complex obtained in Comparative Synthesis Example 1.

Under nitrogen atmosphere, 2.81 g (9.5 mmol) of zinc nitrate hexahydrate, 1.5 g (9.5 mmol) of terephthalic acid, and 0.739 g (4.7 mmol) of 4,4'-bipyridyl were dissolved in 800 mL of a mixed solvent containing N,N-dimethylformamide and ethanol at a volume ratio of 1:1, and the mixture was stirred at 363 K for 48 hours. The precipitated metal complex was recovered by suction filtration and washed three times with methanol. Then, the product was dried at 373 K and 50 Pa for 8 hours to obtain 2.75 g of an intended metal complex (95% of yield). FIG. 11 shows a powder X-ray diffraction pattern of the resulting metal complex.

Comparative Synthesis Example 2

Figure 12:
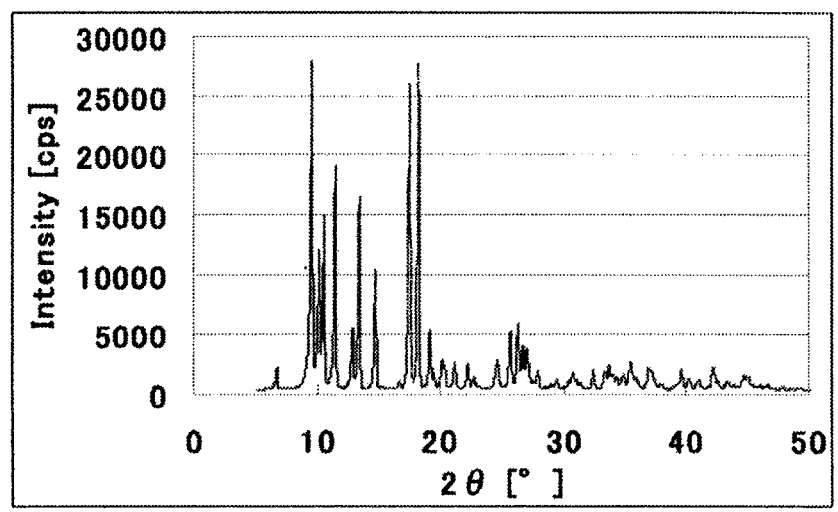
FIG. 12 is a powder X-ray diffraction pattern of the metal complex obtained in Comparative Synthesis Example 2.

Under nitrogen atmosphere, 2.81 g (9.5 mmol) of zinc nitrate hexahydrate, 2.00 g (9.5 mmol) of 2-nitroterephthalic acid, and 0.739 g (4.7 mmol) of 4,4'-bipyridyl were dissolved in 800 mL of a mixed solvent containing N,N-dimethylformamide and ethanol at a volume ratio of 1:1, and the mixture was stirred at 363 K for 48 hours. The precipitated metal complex was recovered by suction filtration and washed three times with methanol. Then, the product was dried at 373 K and 50 Pa for 8 hours to obtain 2.89 g of an intended metal complex (87% of yield). FIG. 12 shows a powder X-ray diffraction pattern of the resulting metal complex.

Comparative Synthesis Example 3

Figure 13:
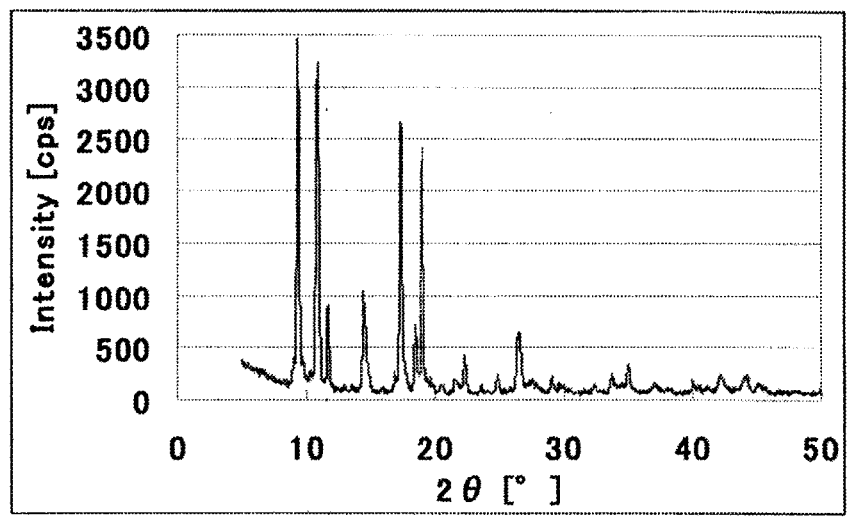
FIG. 13 is a powder X-ray diffraction pattern of the metal complex obtained in Comparative Synthesis Example 3.

1.80 g of the metal complex obtained in Comparative Synthesis Example 1 and 0.203 g of the metal complex obtained in Comparative Synthesis Example 2 were dispersed in 50 mL of methanol and the mixture was stirred at 298 K for one hour. The precipitated metal complex was recovered by suction filtration and washed three times with methanol. Then, the product was dried at 373 K and 50 Pa for 8 hours to obtain 1.98 g of an intended metal complex (99% of yield). FIG. 13 shows a powder X-ray diffraction pattern of the resulting metal complex.

Comparative Synthesis Example 4

Figure 14:
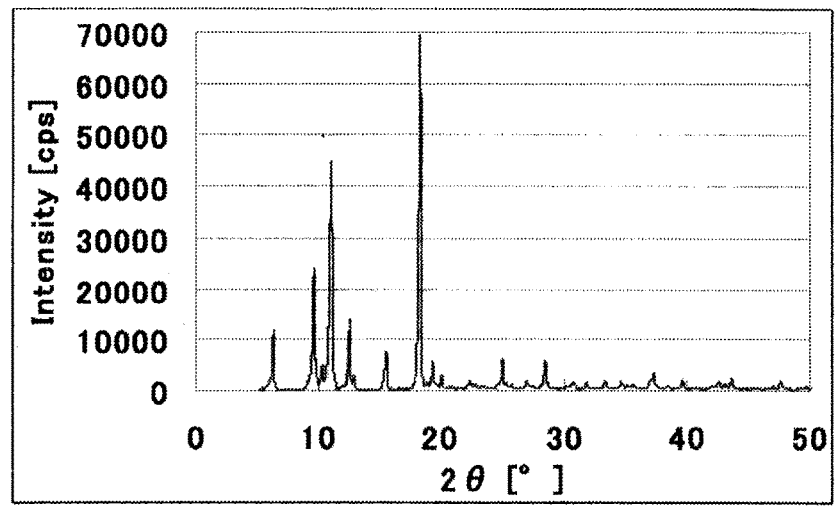
FIG. 14 is a powder X-ray diffraction pattern of the metal complex obtained in Comparative Synthesis Example 4.

Under nitrogen atmosphere, 2.81 g (9.5 mmol) of zinc nitrate hexahydrate, 1.70 g (9.5 mmol) of 2-methylterephthalic acid, and 0.739 g (4.7 mmol) of 4,4'-bipyridyl were dissolved in 800 mL of a mixed solvent containing N,N-dimethylformamide and ethanol at a volume ratio of 1:1, and the mixture was stirred at 363 K for 48 hours. The precipitated metal complex was recovered by suction filtration and washed three times with methanol. Then, the product was dried at 373 K and 50 Pa for 8 hours to obtain 2.72 g of an intended metal complex (89% of yield). FIG. 14 shows a powder X-ray diffraction pattern of the resulting metal complex.

Comparative Synthesis Example 5

Figure 15:
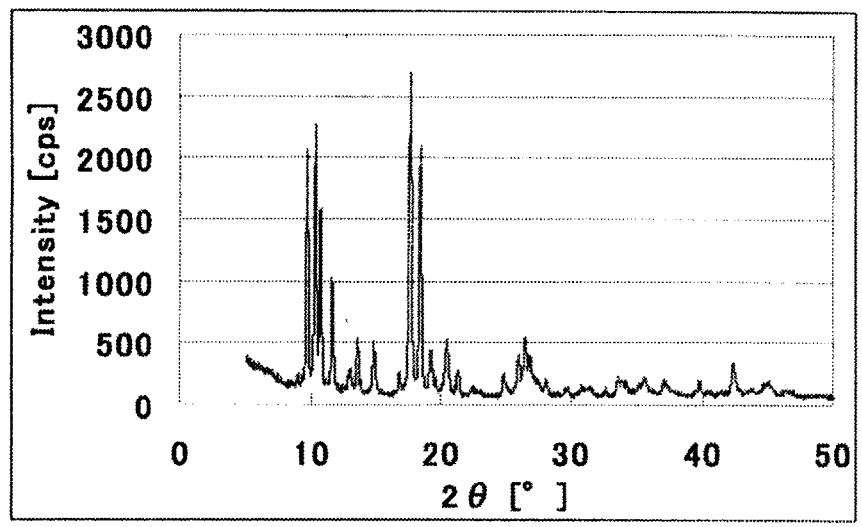
FIG. 15 is a powder X-ray diffraction pattern of the metal complex obtained in Comparative Synthesis Example 5.

Under nitrogen atmosphere, 2.51 g (8.5 mmol) of zinc nitrate hexahydrate, 0.140 g (0.85 mmol) of terephthalic acid, 1.61 g (7.6 mmol) of 2-methylterephthalic acid, and 0.66 g (4.2 mmol) of 4,4'-bipyridyl were dissolved in 100 mL of a mixed solvent containing N,N-dimethylformamide and ethanol at a volume ratio of 1:1, and the mixture was stirred at 363 K for 24 hours. The precipitated metal complex was recovered by suction filtration and washed three times with methanol. Then, the product was dried at 373 K and 50 Pa for 8 hours to obtain 2.63 g of an intended metal complex (89% of yield). FIG. 15 shows a powder X-ray diffraction pattern of the resulting metal complex.

19.9 mg of the resulting metal complexes were dissolved in 1.25 g of a mixed solvent of aqueous ammonia and heavy water, and $^1H$ NMR measurement was performed. As a result of analyzing a spectrum, the molar ratio of terephthalic acid to 2-nitroterephthalic acid (terephthalic acid:2-nitroterephthalic acid) contained in a metal complex was found to be 10:90.

Comparative Synthesis Example 6

Figure 16:
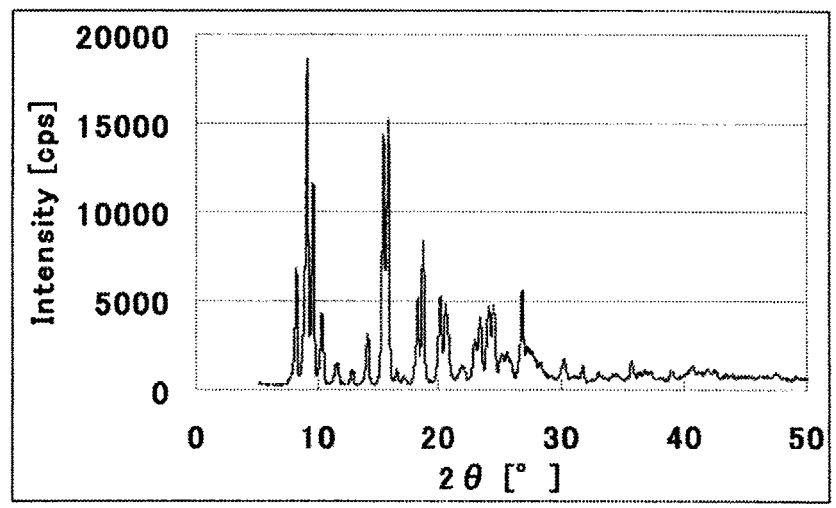
FIG. 16 is a powder X-ray diffraction pattern of the metal complex obtained in Comparative Synthesis Example 6.

Under nitrogen atmosphere, 12.6 g (42 mmol) of zinc nitrate hexahydrate, 0.829 g (4.2 mmol) of 5-methoxyisophthalic acid, 8.03 g (38 mmol) of 5-nitroisophthalic acid, and 6.60 g (42 mmol) of 4,4'-bipyridyl were dissolved in 200 mL of N,N-dimethylformamide, and the mixture was stirred at 393 K for 24 hours. The precipitated metal complex was recovered by suction filtration and washed three times with methanol. Then, the product was dried at 373 K and 50 Pa for 8 hours to obtain 16.1 g of an intended metal complex (89% of yield). FIG. 16 shows a powder X-ray diffraction pattern of the resulting metal complex.

Table 1 shows the metal complexes obtained in the Synthesis Examples 1 to 6 and the Comparative Synthesis Examples 1 to 6.

TABLE 1

Figure 8:
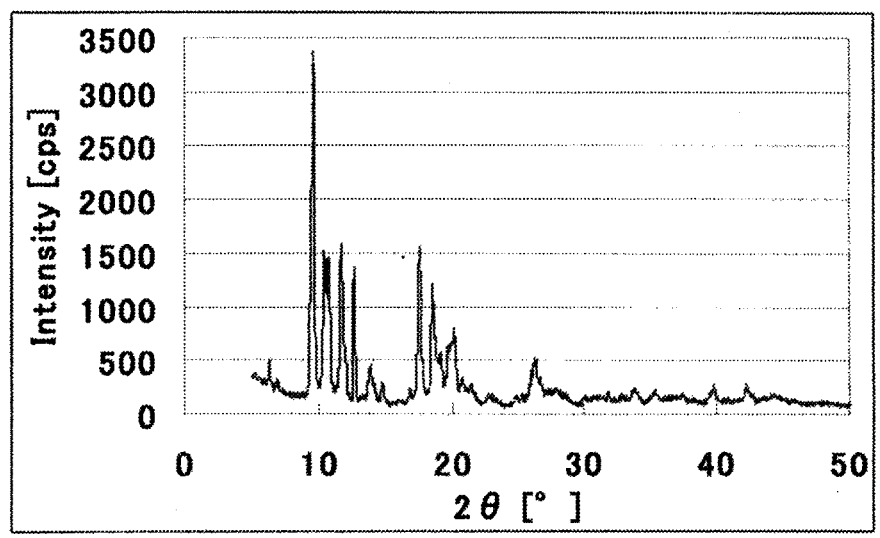
FIG. 8 is a powder X-ray diffraction pattern of the metal complex obtained in Synthesis Example 4.

| | Dicarboxylic Acid (I) | | Molar Ratio | | Powder X-ray Diffraction |
|---|---|---|---|---|---|
| | (I-1) | (I-2) | (I-1) | (I-2) | |
| Synthesis Example 1 | Terephthalic acid | 2-Nitroterephthalic acid | 33 | 67 | FIG. 5 |
| Synthesis Example 2 | Terephthalic acid | 2-Nitroterephthalic acid | 89 | 11 | FIG. 6 |
| Synthesis Example 3 | 2-Methylterephthalic acid | 2-Nitroterephthalic acid | 50 | 50 | FIG. 7 |
| Synthesis Example 4 | Terephthalic acid | 2-Nitroterephthalic acid | 50 | 50 | FIG. 8 |
| Synthesis Example 5 | Terephthalic acid | 2-Nitroterephthalic acid | 70 | 30 | FIG. 9 |
| Synthesis Example 6 | Terephthalic acid | 2-Nitroterephthalic acid | 30 | 70 | FIG. 10 |
| Comparative Synthesis Example 1 | Terephthalic acid | — | 100 | 0 | FIG. 11 |
| Comparative Synthesis Example 2 | — | 2-Nitroterephthalic acid | 0 | 100 | FIG. 12 |
| Comparative Synthesis Example 3 | Mixture of the complex of terephthalic acid and the complex of 2-nitroterephthalic acid | | — | — | FIG. 13 |
| Comparative Synthesis Example 4 | 2-Methylterephthalic acid | — | 100 | 0 | FIG. 14 |
| Comparative Synthesis Example 5 | Terephthalic acid | 2-Nitroterephthalic acid | 10 | 90 | FIG. 15 |
| Comparative Synthesis Example 6 | 5-Methoxyisophthalic acid | 5-Nitroisophthalic acid | — | — | FIG. 16 |

Comparison of FIG. 5, FIG. 6, FIG. 8, FIG. 9, FIG. 11, FIG. 12, FIG. 13, and FIG. 15 reveals that the metal complexes obtained in Synthesis Example 1, Synthesis Example 2, Synthesis Example 4, Synthesis Example 5, and Example 5 of comparison composition are different from the mixture of the metal complexes obtained in Comparative Synthesis Example 1 and Comparative Synthesis Example 2.

Comparison of FIG. 7, FIG. 12 and FIG. 14 reveals that the metal complex obtained in Synthesis Example 3 is different from the mixture of the metal complexes obtained in Comparative Synthesis Example 1 and Comparative Synthesis Example 4.

Example 1

Figure 17:
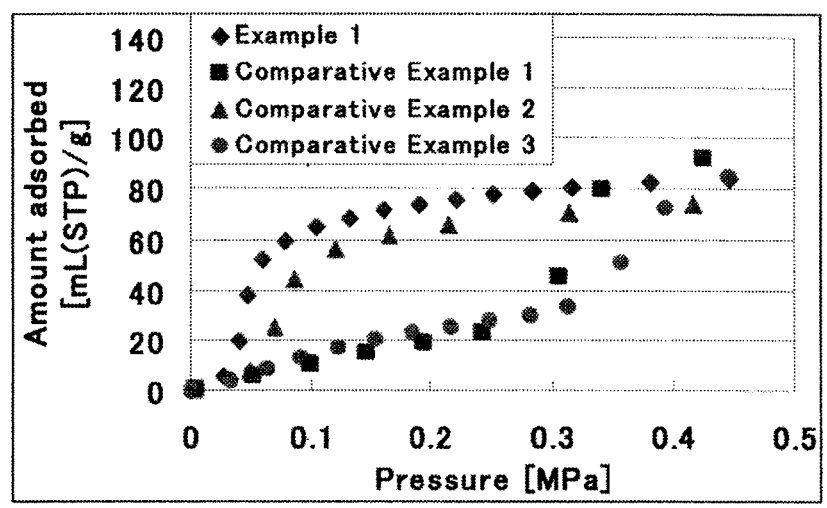
FIG. 17 is a result of measuring the adsorption isotherm at 273 K of carbon dioxide with a volumetric method, regarding the metal complex obtained in Synthesis Example 1, Comparative Synthesis Example 1, Comparative Synthesis Example 2, and Comparative Synthesis Example 3.

For the metal complex obtained in Synthesis Example 1, the adsorption amount of carbon dioxide at 273 K was measured according to the volumetric method, and the adsorption isotherm was created. The result is shown in FIG. 17 (Example 1).

Comparative Example 1

For the metal complex obtained in Comparative Synthesis Example 1, the adsorption amount of carbon dioxide at 273 K was measured according to the volumetric method, and the adsorption isotherm was created. The result is shown in FIG. 17 (Comparative Example 1).

Comparative Example 2

For the metal complex obtained in Comparative Synthesis Example 2, the adsorption amount of the carbon dioxide at 273 K was measured according to the volumetric method, and the adsorption isotherm was created. The result is shown in FIG. 17 (Comparative Example 2).

Comparative Example 3

For the metal complex obtained in Comparative Example 3, the adsorption amount of carbon dioxide at 273 K was measured according the volumetric method, and adsorption isotherm was created. The result is shown in FIG. 17 (Comparative Example 3)

It is clear from FIG. 17 that, since the metal complex obtained in Synthesis Example 1 that satisfies the constituent requirements of the invention adsorbs carbon dioxide with an increase in pressure and the adsorption amount of carbon dioxide of the metal complex obtained in Synthesis Example 1 at a lower pressure zone is greater than that of the metal complexes obtained in Comparative Synthesis Examples 1, 2, and 3, which do not satisfy the constituent requirements of the present invention, the metal complex of the invention is excellent as an adsorbent material of carbon dioxide.

Example 2

Figure 18:
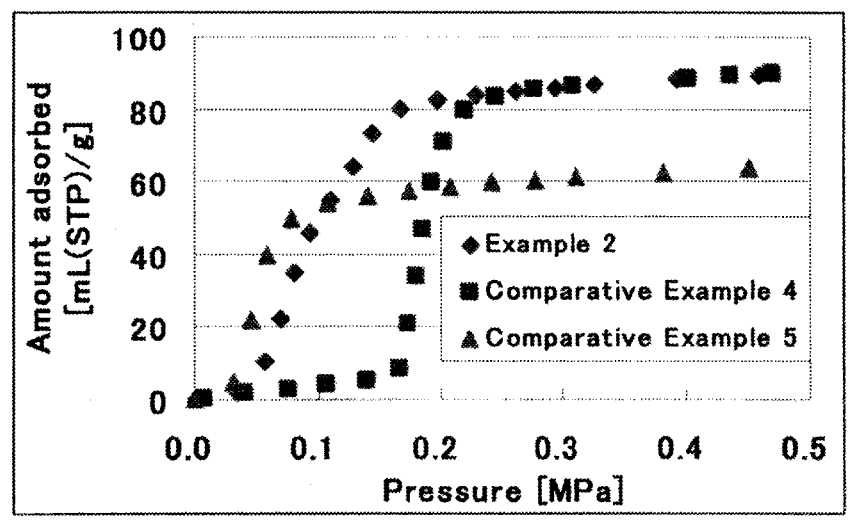
FIG. 18 is a result of measuring the adsorption isotherm at 273 K of ethylene with a volumetric method, regarding the metal complex obtained in Synthesis Example 2, Comparative Synthesis Example 1, Comparative Synthesis Example 2, and Comparative Synthesis Example 3.

For the metal complex obtained in Synthesis Example 2, the adsorption amount of ethylene at 273 K was measured according to the volumetric method, and the adsorption isotherm was created. The result is shown in FIG. 18 (Example 2).

Comparative Example 4

For the metal complex obtained in Comparative Synthesis Example 1, the adsorption amount of ethylene at 273 K was measured according to the volumetric method, and the adsorption isotherm was created. The result is shown in FIG. 18 (Comparative Example 4).

Comparative Example 5

For the metal complex obtained in Comparative Synthesis Example 2, the adsorption amount of ethylene at 273 K was measured according to the volumetric method, and the adsorption isotherm was created. The result is shown in FIG. 18 (Comparative Example 5).

It is clear from FIG. 18 that the metal complex of the invention is excellent as an adsorbent material of ethylene because the metal complex obtained in Synthesis Example 2 that satisfies the constituent requirements of the invention adsorbs ethylene with an increase in pressure and the adsorption amount of ethylene of the metal complex obtained in Synthesis Example 1 is greater than that of the metal complexes obtained in Comparative Synthesis Examples 1 and 2, which do not satisfy the constituent requirements of the present invention, particularly prominent at a lower pressure zone.

Example 3

Figure 19:
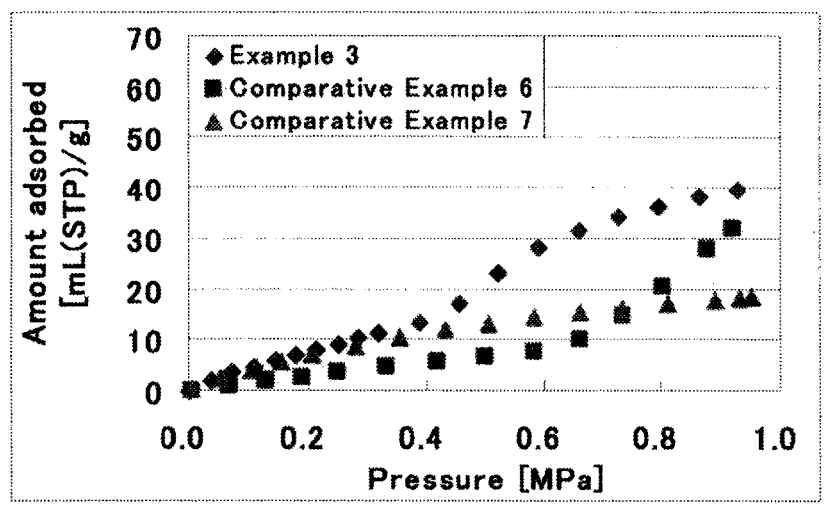
FIG. 19 is a result of measuring the adsorption isotherm at 273 K of ethylene with a volumetric method, regarding the metal complex obtained in Synthesis Example 3, Comparative Synthesis Example 2, and Comparative Synthesis Example 4.

For the metal complex obtained in Synthesis Example 3, the adsorption amount of methane at 273 K was measured according to the volumetric method, and the adsorption isotherm was created. The result is shown in FIG. 19 (Example 3).

Comparative Example 6

For the metal complex obtained in Comparative Synthesis Example 2, the adsorption amount of methane at 273 K was measured according to the volumetric method, and the adsorption isotherm was created. The result is shown in FIG. 19 (Comparative Example 6).

Comparative Example 7

For the metal complex obtained in Comparative Synthesis Example 4, the adsorption amount of methane at 273 K was measured according to the volumetric method, and the adsorption isotherm was created. The result is shown in FIG. 19 (Comparative Example 7).

It is clear from FIG. 19 that the metal complex of the invention is excellent as an adsorbent material of ethylene because the metal complex obtained in Synthesis Example 1 that satisfies the constituent requirements of the invention adsorbs methane with an increase in pressure, and the adsorption amount of methane of the metal complex obtained in Synthesis Example 1 is greater than that of the metal complexes obtained in Comparative Synthesis Examples 1 and 4 that do not satisfy the constituent requirements of the present invention.

Example 4

Figure 20:
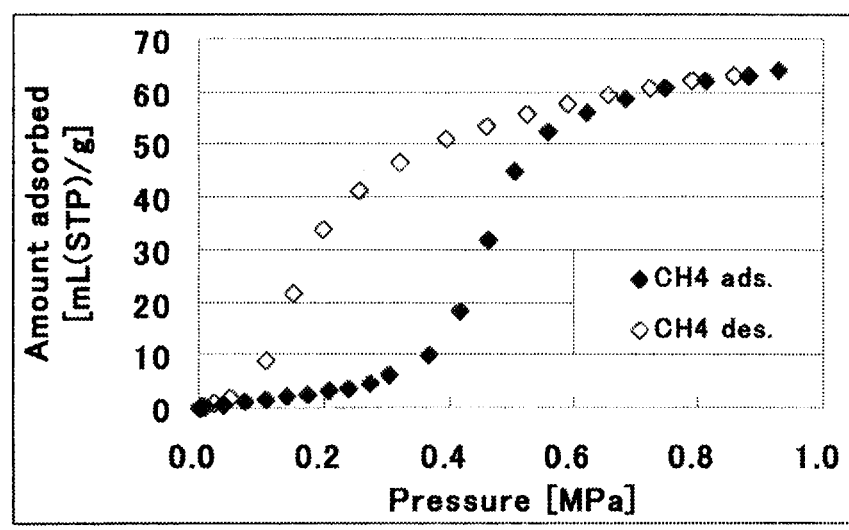
FIG. 20 is a result for measuring the adsorption/desorption isotherms at 273 K of methane with a volumetric method, regarding the metal complex obtained in Synthesis Example 1.

For the metal complex obtained in Synthesis Example 1, the adsorption and desorption amounts of methane at 273 K were measured according to the volumetric method, and the adsorption and desorption isotherms were created. The result is shown in FIG. 20.

Example 5

Figure 21:
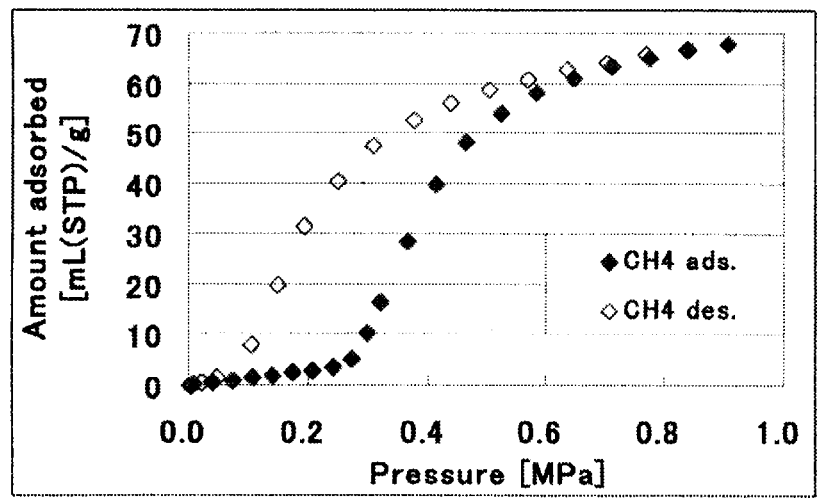
FIG. 21 is a result for measuring the adsorption/desorption isotherms at 273 K of methane with a volumetric method, regarding the metal complex obtained in Synthesis Example 4.

For the metal complex obtained in Synthesis Example 4, the adsorption and desorption amounts of methane at 273 K were measured according to the volumetric method, and the adsorption and desorption isotherms were created. The result is shown in FIG. 21.

Example 6

Figure 22:
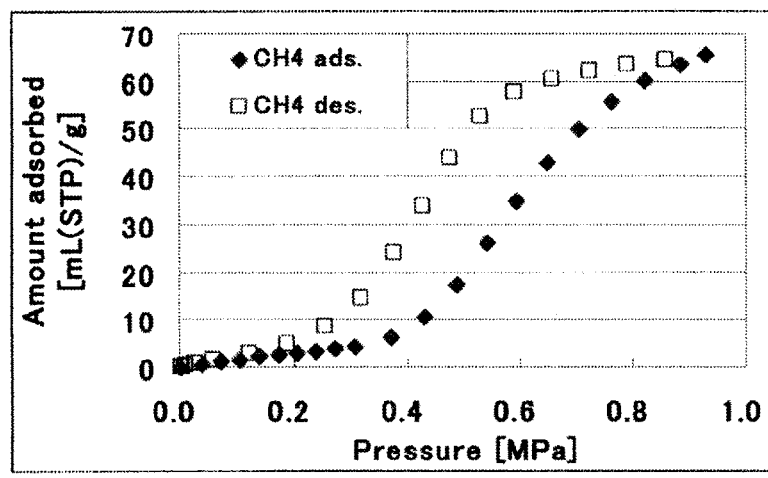
FIG. 22 is a result for measuring the adsorption/desorption isotherm at 273 K of methane with a volumetric method, regarding the metal complex obtained in Synthesis Example 5.

For the metal complex obtained in Synthesis Example 5, the adsorption and desorption amounts of methane at 273 K were measured with the volumetric method, and the adsorption and desorption isotherms were created. The result is shown in FIG. 22.

Comparative Example 8

Figure 23:
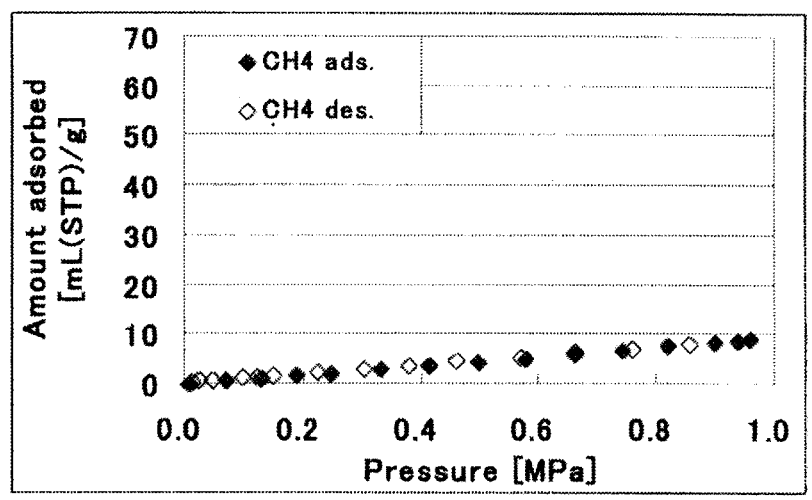
FIG. 23 is a result for measuring the adsorption/desorption isotherms at 273 K of methane with a volumetric method, regarding the metal complex obtained in Comparative Synthesis Example 1.

For the metal complex obtained in Comparative Synthesis Example 1, the adsorption and desorption amounts of methane at 273 K were measured with the volumetric method, and the adsorption and desorption isotherms were created. The result is shown in FIG. 23.

Comparative Example 9

Figure 24:
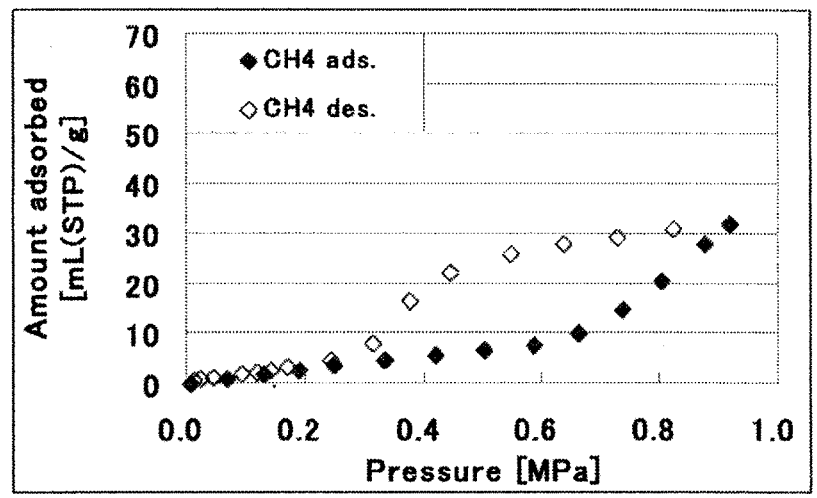
FIG. 24 is a result for measuring the adsorption/desorption isotherms at 273 K of methane with a volumetric method, regarding the metal complex obtained in Comparative Synthesis Example 2.

For the metal complex obtained in Comparative Synthesis Example 2, the adsorption and desorption amounts of methane at 273 K were measured with the volumetric method, and the adsorption and desorption isotherms were created. The result is shown in FIG. 24.

Comparative Example 10

Figure 25:
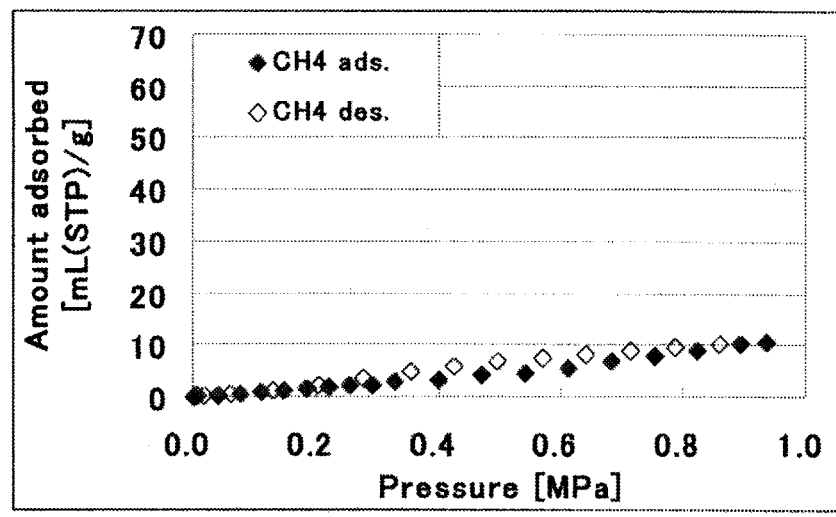
FIG. 25 is a result for measuring the adsorption/desorption isotherms at 273 K of methane with a volumetric method, regarding the metal complex obtained in Comparative Synthesis Example 3.

For the metal complex obtained in Comparative Synthesis Example 3, the adsorption and desorption amounts of methane at 273 K were measured with the volumetric method, and the adsorption and desorption isotherms were created. The result is shown in FIG. 25.

Comparative Example 11

Figure 26:
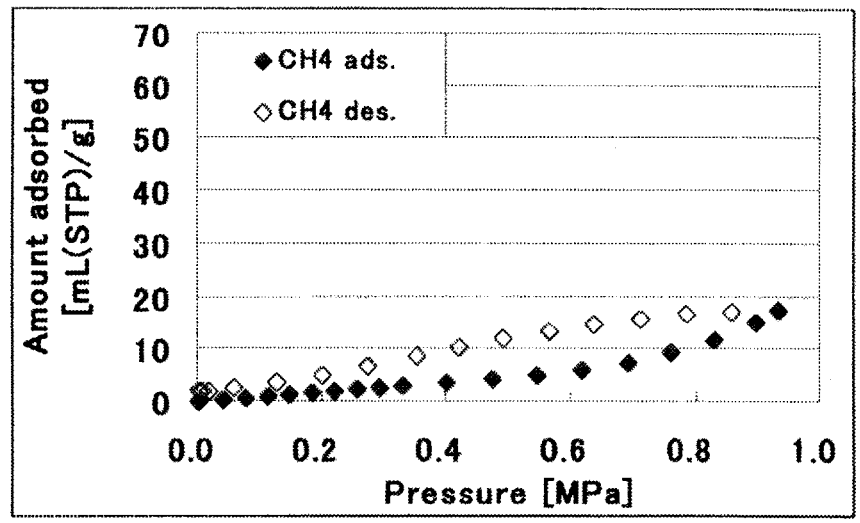
FIG. 26 is a result for measuring the adsorption/desorption isotherms at 273 K of methane with a volumetric method, regarding the metal complex obtained in Comparative Synthesis Example 5.

For the metal complex obtained in Comparative Example 5, the adsorption and desorption amounts of methane at 273 K were measured with the volumetric method, and the adsorption and desorption isotherms were created. The result is shown in FIG. 26.

Comparison of FIG. 20, FIG. 21 and FIG. 22, and FIG. 23, FIG. 24, FIG. 25 and FIG. 26 reveals that the metal complexes obtained in Synthesis Example 1, Synthesis Example 4, and Synthesis Example 5 that satisfy the constituent requirements of the invention adsorbs methane with an increase in pressure, and the adsorption amounts of methane are greater than those of Comparative Synthesis Example 1, Comparative Synthesis Example 3, and Comparative Synthesis Example 5, which do not satisfy the constituent requirements of the invention. In addition, the metal complexes obtained in Synthesis Example 1, Synthesis Example 4, and Synthesis Example 5 release 85% or more of the adsorbed methane with a decrease in pressure without decrease in pressure to 0.1 MPa or lower. Thus, it is clear that the metal complexes of the invention are excellent as a storage material of methane, and application to fuel storage tanks of gas-fueled automobiles can be expected.

Example 7

Figure 27:
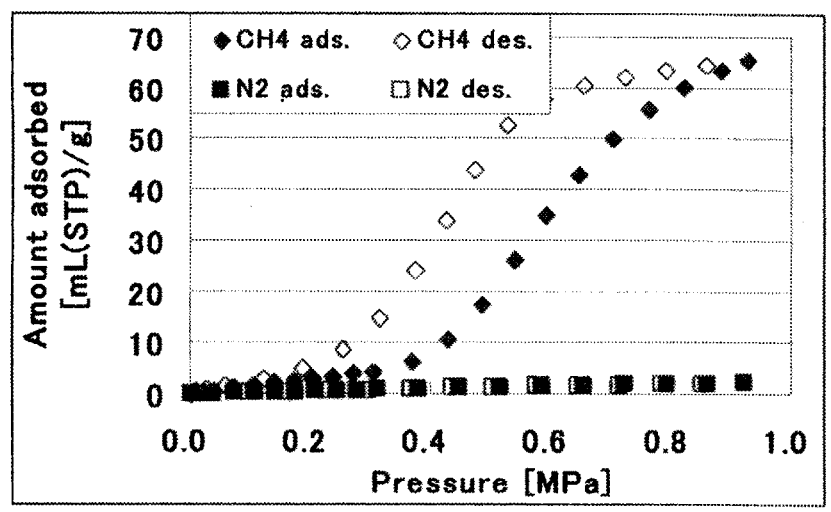
FIG. 27 is a result for measuring the adsorption/desorption isotherms at 273 K of methane and nitrogen with a volumetric method, regarding the metal complex obtained in Synthesis Example 5.

For the metal complex obtained in Synthesis Example 5, the amounts of adsorption and desorption of methane and nitrogen at 273 K were measured according to the volumetric method, and the adsorption and desorption isotherms were created. The result is shown in FIG. 27.

Comparative Example 12

For the metal complex obtained in Comparative Synthesis Example 1, the amounts of adsorption and desorption of methane and nitrogen at 273 K were measured according to the volumetric method, and the adsorption and desorption isotherms were created. The result is shown in FIG. 28.

Comparative Example 13

For the metal complex obtained in Comparative Synthesis Example 2, the amounts of adsorption and desorption of methane and nitrogen at 273 K were measured according to the volumetric method, and the adsorption and desorption isotherms were created. The result is shown in FIG. 29.

Figure 28:
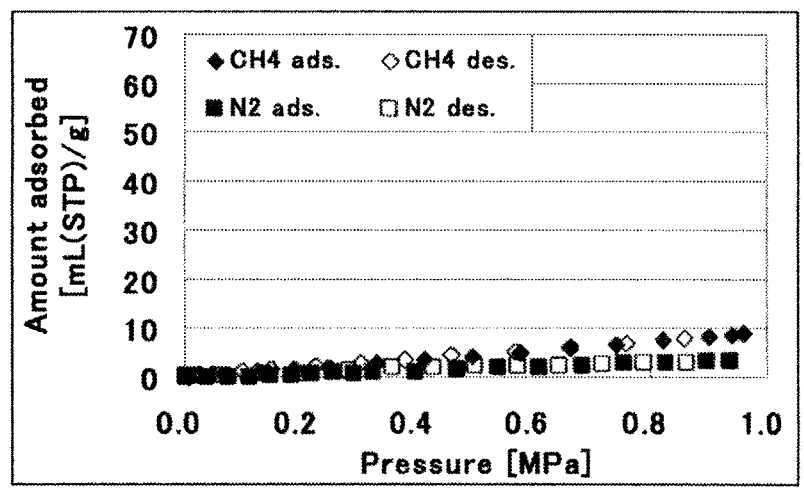
FIG. 28 is a result for measuring the adsorption/desorption isotherms at 273 K of methane and nitrogen with a volumetric method, regarding the metal complex obtained in Comparative Synthesis Example 1.
Figure 29:
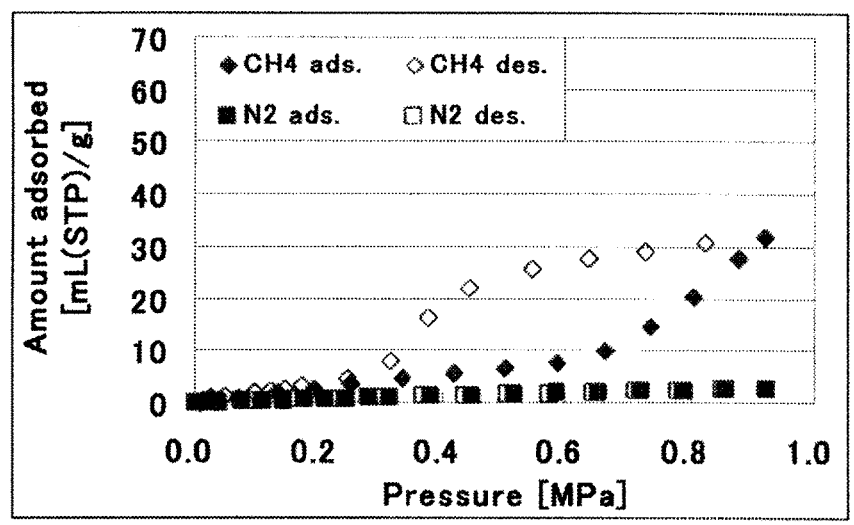
FIG. 29 is a result for measuring the adsorption/desorption isotherms at 273 K of methane and nitrogen with a volumetric method, regarding the metal complex obtained in Comparative Synthesis Example 2.

Comparison of FIG. 27, FIG. 28, and FIG. 29 reveals that the metal complex obtained in Synthesis Example 5 that satisfies the constituent requirements of the invention selectively adsorbs methane with an increase in pressure, and the adsorption amount of methane is greater than that of Comparative Synthesis Example 1 and Comparative Synthesis Example 2, which do not satisfy the constituent requirements of the invention. In addition, the metal complex obtained in Synthesis Example 5 releases methane with a decrease in pressure. Thus, it is clear that the metal complex of the invention is excellent as a separating material of methane and nitrogen.

Example 8

For the metal complex obtained in Synthesis Example 2, the amounts of adsorption and desorption of ethane and methane at 273 K were measured according to the volumetric method, and the adsorption and desorption isotherms were created. The result is shown in FIG. 30.

Comparative Example 14

For the metal complex obtained in Comparative Synthesis Example 2, the amounts of adsorption and desorption of ethane and methane at 273 K were measured according to the volumetric method, and the adsorption and desorption isotherms were created. The result is shown in FIG. 31.

Figure 30:
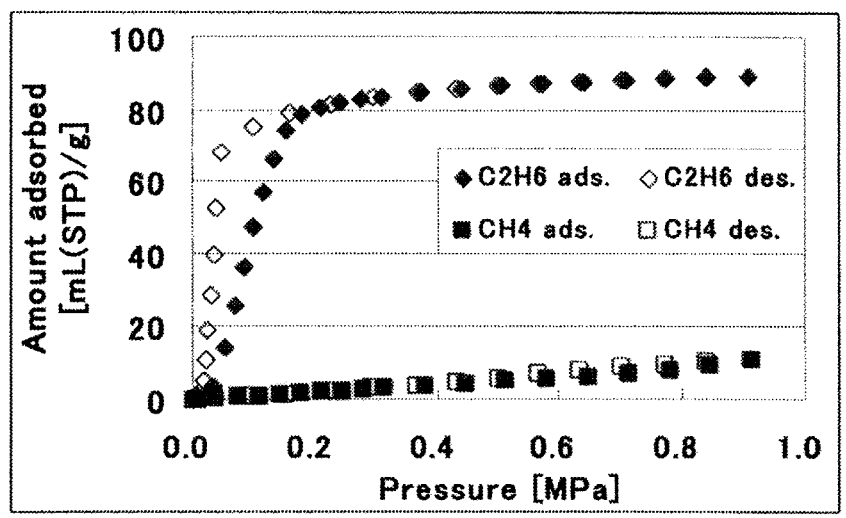
FIG. 30 is a result for measuring the adsorption/desorption isotherms at 273 K of ethane and methane with a volumetric method, regarding the metal complex obtained in Synthesis Example 2.
Figure 31:
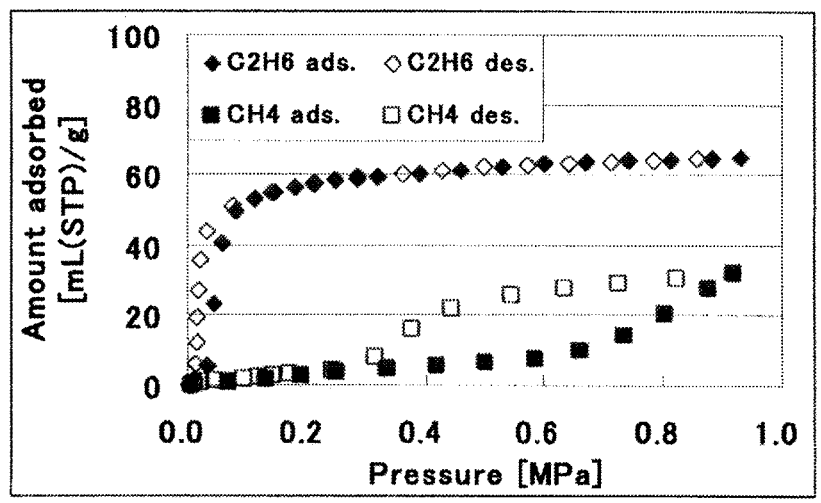
FIG. 31 is a result for measuring the adsorption/desorption isotherms at 273 K of ethane and methane with a volumetric method, regarding the metal complex obtained in Comparative Synthesis Example 2.

Comparison of FIG. 30 and FIG. 31 reveals that the metal complex obtained in Synthesis Example 2 that satisfies the constituent requirements of the invention selectively adsorbs ethane with an increase in pressure, and the adsorption amount of ethane is greater than that of Comparative Synthesis Example 2, which does not satisfy the constituent requirements of the invention. In addition, the metal complex obtained in Example 2 releases ethane with a decrease in pressure. Thus, it is clear that the metal complex of the invention is excellent as a separating material of ethane and methane.

Example 9

For the metal complex obtained in Synthesis Example 2, the amounts of adsorption and desorption of carbon dioxide and nitrogen at 273 K were measured according to the volumetric method, and the adsorption and desorption isotherms were created. The result is shown in FIG. 32.

Comparative Example 15

For the metal complex obtained in Comparative Example 2, the amounts of adsorption and desorption of carbon dioxide and nitrogen at 273 K were measured with the volumetric method, and the adsorption and desorption isotherms were created. The result is shown in FIG. 33.

Figure 32:
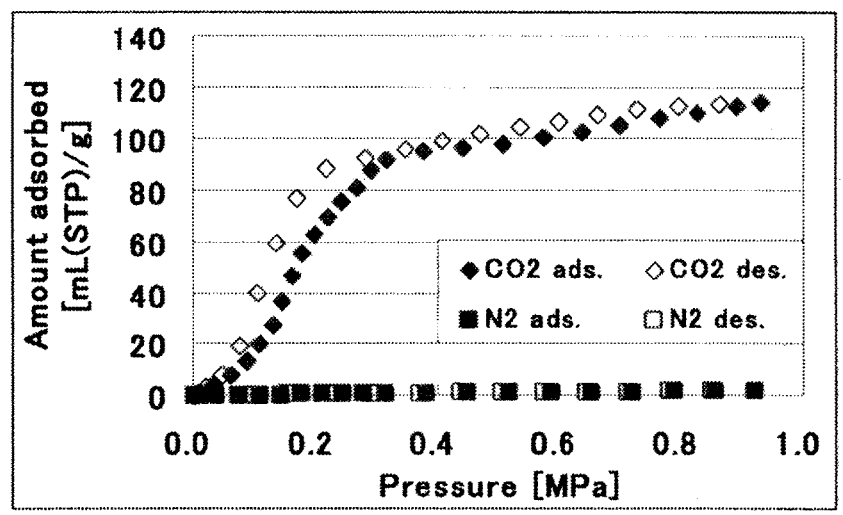
FIG. 32 is a result for measuring the adsorption/desorption isotherms at 273 K of carbon dioxide and nitrogen with a volumetric method, regarding the metal complex obtained in Synthesis Example 2.
Figure 33:
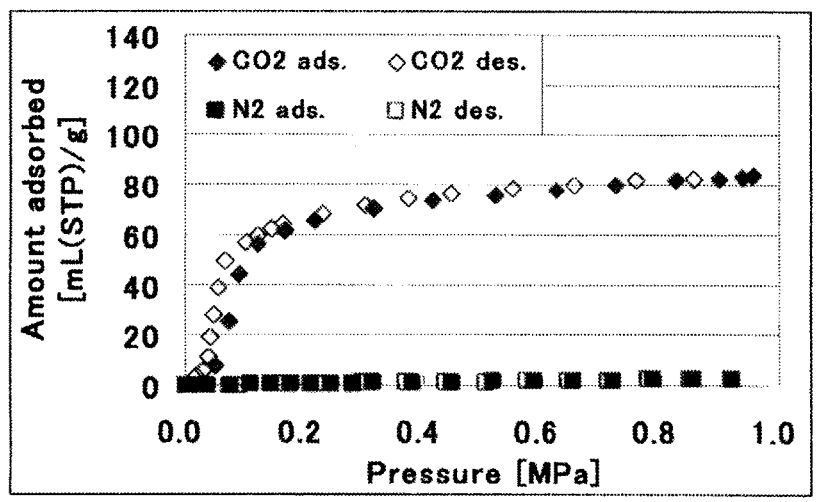
FIG. 33 is a result for measuring the adsorption/desorption isotherms at 273 K of carbon dioxide and nitrogen with a volumetric method, regarding the metal complex obtained in Comparative Synthesis Example 2.

Comparison of FIG. 32 and FIG. 33 reveals that the metal complex obtained in Synthesis Example 2 that satisfies the constituent requirements of the invention selectively adsorbs carbon dioxide with an increase in pressure, and the adsorption amount of carbon dioxide is greater than that of Comparative Synthesis Example 2, which does not satisfy the constituent requirements of the invention. In addition, the metal complex obtained in Synthesis Example 2 releases carbon dioxide with a decrease in pressure. Thus, it is clear that the metal complex of the invention is excellent as a separating material of nitrogen and carbon dioxide.

Example 10

Figure 34:
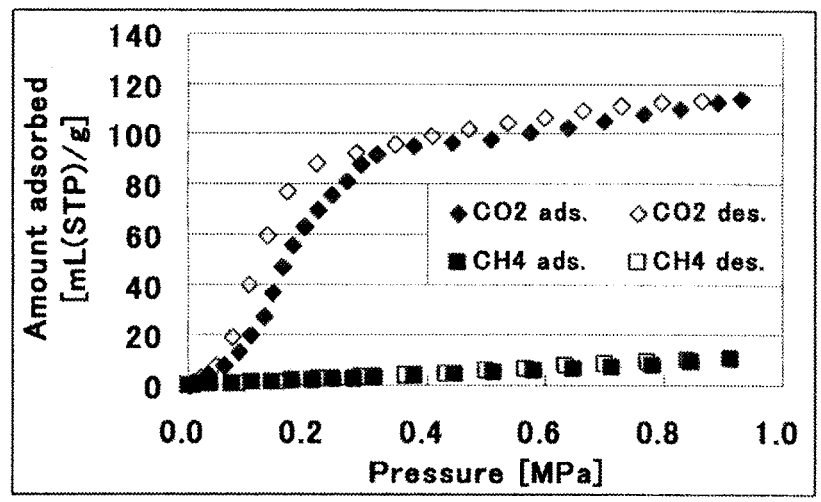
FIG. 34 is a result for measuring the adsorption/desorption isotherms at 273 K of carbon dioxide and methane with a volumetric method, regarding the metal complex obtained in Synthesis Example 2.

For the metal complex obtained in Synthesis Example 2, the amounts of adsorption and desorption of carbon dioxide and methane at 273 K were measured accordance with the volumetric method, and the adsorption and desorption isotherms were created. The result is shown in FIG. 34.

Example 11

Figure 35:
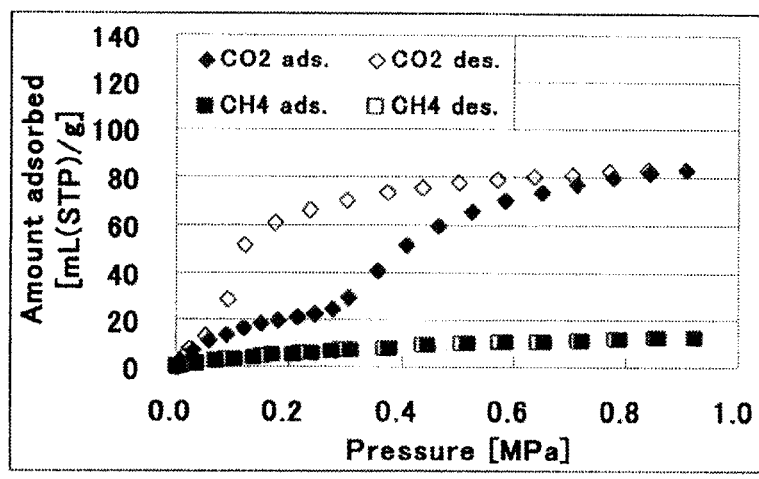
FIG. 35 is a result for measuring the adsorption/desorption isotherms at 273 K of carbon dioxide and methane with a volumetric method, regarding the metal complex obtained in Synthesis Example 6.

For the metal complex obtained in Synthesis Example 6, the amounts of adsorption and desorption of carbon dioxide and methane at 273 K were measured with the volumetric method, and the adsorption and desorption isotherms were created. The result is shown in FIG. 35.

Comparative Example 16

Figure 36:
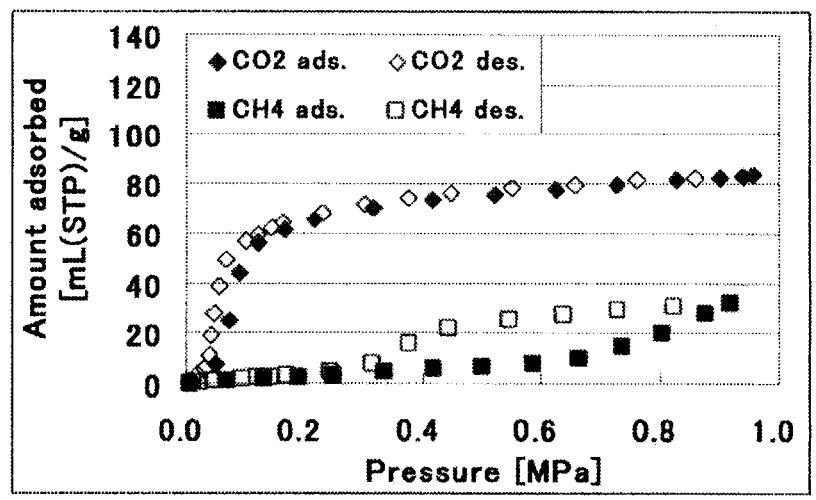
FIG. 36 is a result for measuring the adsorption/desorption isotherms at 273 K of carbon dioxide and methane with a volumetric method, regarding the metal complex obtained in Comparative Synthesis Example 2.

For the metal complex obtained in Comparative Synthesis Example 2, the amounts of adsorption and desorption of carbon dioxide and methane at 273 K were measured according to the volumetric method, and the adsorption and desorption isotherms were created. The result is shown in FIG. 36.

Comparative Example 17

Figure 37:
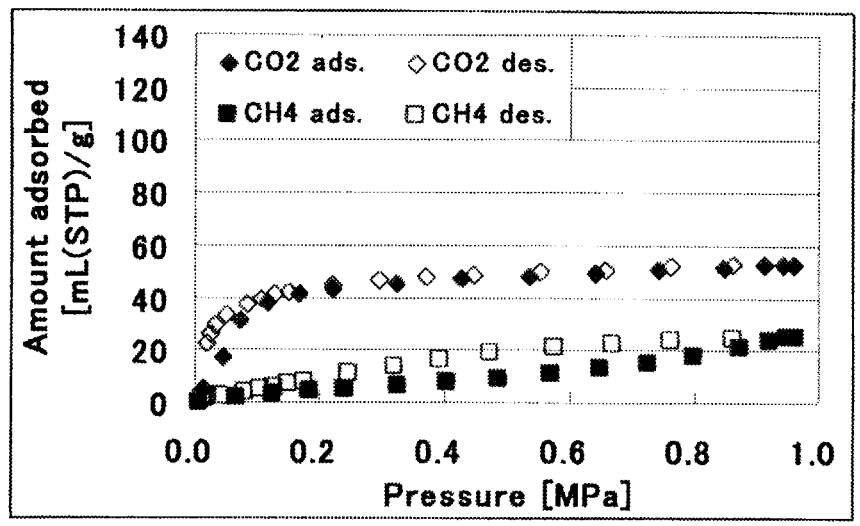
FIG. 37 is a result for measuring the adsorption/desorption isotherms at 273 K of carbon dioxide and methane with a volumetric method, regarding the metal complex obtained in Comparative Synthesis Example 6.

For the metal complex obtained in Comparative Synthesis Example 6, the amounts of adsorption and desorption of carbon dioxide and methane at 273 K were measured according to the volumetric method, and the adsorption and desorption isotherms were created. The result is shown in FIG. 37.

Comparison of FIG. 34 and FIG. 35, FIG. 36, and FIG. 37 reveals that the metal complexes obtained in Synthesis Example 2 and Synthesis Example 6 that satisfy the constituent requirements of the invention selectively adsorb carbon dioxide with an increase in pressure, and the adsorption amounts of carbon dioxide are greater than those of the metal complexes obtained in the Comparative Synthesis Example 2 and Comparative Synthesis Example 6, which do not satisfy the constituent requirements of the invention. In addition, the metal complexes obtained in Synthesis Example 2 and Synthesis Example 6 release carbon dioxide with a decrease in pressure.

Thus, it is clear that the metal complex of the invention is excellent as a separating material of methane and carbon dioxide.

Example 12

For the metal complex obtained in Synthesis Example 2, using a mixed gas of methane and carbon dioxide with a ratio of methane:carbon dioxide of 60:40 by volume ratio, the breakthrough curve at 273 K, 0.8 MPa, and at a space velocity of 6 min$^{-1}$ was measured, and the gas separation performance was evaluated. The result is shown in FIG. 38.

Figure 38:
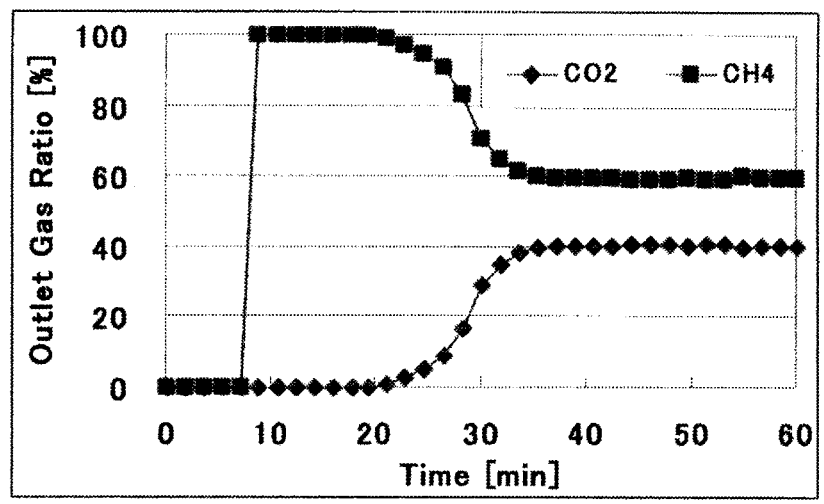
FIG. 38 is a result for measuring a breakthrough curve at 273 K, 0.8 MPa, and space, velocity of 6 min$^{-1}$ using a mixed gas of methane and carbon dioxide at the ratio of methane to carbon dioxide of 60 to 40.

It can be understood from FIG. 38 that the metal complex obtained in Synthesis Example 2 that satisfies the constituent requirements of the invention preferentially adsorbs carbon dioxide and enriches methane up to 99.5% or higher. Since the breakthrough time (the period until carbon dioxide is detected in an outlet gas) is long and only methane can be recovered during that period, it is clear that the metal complex of the invention can be used as a separating material of methane and carbon dioxide. In addition, it is clear from FIG. 34 that, since the metal complex of the invention releases the adsorbed carbon dioxide with a decrease in pressure, it can be used as a separating material for use in a pressure swing adsorption process.

Example 13

For the metal complex obtained in Synthesis Example 2, the amounts of adsorption and desorption of carbon dioxide and methane at 313 K were measured according to the volumetric method, and the adsorption and desorption isotherms were created. The result is shown in FIG. 39.

Figure 39:
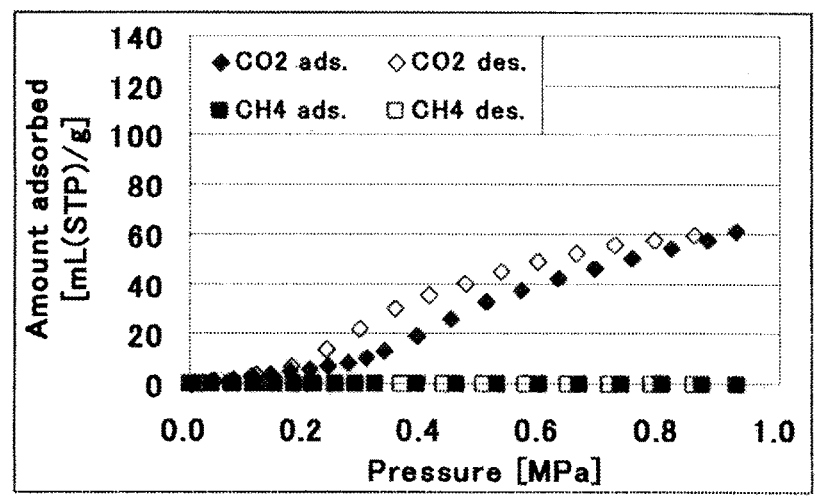
FIG. 39 is a result for measuring the adsorption/desorption isotherms at 313 K of carbon dioxide and methane with a volumetric method, regarding the metal complex obtained in Synthesis Example 2.

It is clear from comparison of FIG. 34 and FIG. 39 that, since the adsorption starting pressure of the metal complex obtained in Synthesis Example 2 that satisfies the constituent requirements of the invention depends on the temperature and is controllable, this metal complex can be used as a separating material for use in a temperature swing adsorption process.

Table 2 shows the results of Examples 1 to 13 and Comparative Examples 1 to 17.

TABLE 2

| | Metal Complex | Adsorption/Desorption Gas | Measured Temperature (K) | Result |
|---|---|---|---|---|
| Example 1 | Synthesis Example 1 | $CO_2$ adsorption | 273 | FIG. 17 |
| Example 2 | Synthesis Example 2 | Ethylene adsorption | 273 | FIG. 18 |
| Example 3 | Synthesis Example 3 | Methane adsorption | 273 | FIG. 19 |
| Example 4 | Synthesis Example 1 | Methane adsorption and desorption | 273 | FIG. 20 |
| Example 5 | Synthesis Example 4 | Methane adsorption and desorption | 273 | FIG. 21 |
| Example 6 | Synthesis Example 5 | Methane adsorption and desorption | 273 | FIG. 22 |
| Example 7 | Synthesis Example 5 | Methane/$N_2$ adsorption and desorption | 273 | FIG. 27 |
| Example 8 | Synthesis Example 2 | Ethane/methane adsorption and desorption | 273 | FIG. 30 |
| Example 9 | Synthesis Example 2 | $CO_2/N_2$ adsorption and desorption | 273 | FIG. 32 |
| Example 10 | Synthesis Example 2 | $CO_2$/methane adsorption and desorption | 273 | FIG. 34 |
| Example 11 | Synthesis Example 6 | $CO_2$/methane adsorption and desorption | 273 | FIG. 35 |
| Example 12 | Synthesis Example 2 | $CO_2$/methane adsorption and desorption | 273 | FIG. 38 |

TABLE 2-continued

| | Metal Complex | Adsorption/Desorption Gas | Measured Temperature (K) | Result |
|---|---|---|---|---|
| Example 13 | Synthesis Example 2 | CO$_2$/methane adsorption and desorption | 313 | FIG. 39 |
| Comparative Example 1 | Comparative Synthesis Example 1 | CO$_2$ adsorption | 273 | FIG. 17 |
| Comparative Example 2 | Comparative Synthesis Example 2 | CO$_2$ adsorption | 273 | FIG. 17 |
| Comparative Example 3 | Comparative Synthesis Example 3 | CO$_2$ adsorption | 273 | FIG. 17 |
| Comparative Example 4 | Comparative Synthesis Example 1 | Ethylene adsorption | 273 | FIG. 18 |
| Comparative Example 5 | Comparative Synthesis Example 2 | Ethylene adsorption | 273 | FIG. 18 |
| Comparative Example 6 | Comparative Synthesis Example 2 | Methane adsorption | 273 | FIG. 19 |
| Comparative Example 7 | Comparative Synthesis Example 4 | Methane adsorption | 273 | FIG. 19 |
| Comparative Example 8 | Comparative Synthesis Example 1 | Methane adsorption and desorption | 273 | FIG. 23 |
| Comparative Example 9 | Comparative Synthesis Example 2 | Methane adsorption and desorption | 273 | FIG. 24 |
| Comparative Example 10 | Comparative Synthesis Example 3 | Methane adsorption and desorption | 273 | FIG. 25 |
| Comparative Example 11 | Comparative Synthesis Example 5 | Methane adsorption and desorption | 273 | FIG. 26 |
| Comparative Example 12 | Comparative Synthesis Example 1 | Methane/N$_2$ adsorption and desorption | 273 | FIG. 28 |
| Comparative Example 13 | Comparative Synthesis Example 2 | Methane/N$_2$ adsorption and desorption | 273 | FIG. 29 |
| Comparative Example 14 | Comparative Synthesis Example 2 | Ethane/methane adsorption and desorption | 273 | FIG. 31 |
| Comparative Example 15 | Comparative Synthesis Example 2 | CO$_2$/N$_2$ adsorption and desorption | 273 | FIG. 33 |
| Comparative Example 16 | Comparative Synthesis Example 2 | CO$_2$/methane adsorption and desorption | 273 | FIG. 36 |
| Comparative Example 17 | Comparative Synthesis Example 6 | CO$_2$/methane adsorption and desorption | 273 | FIG. 37 |

DESCRIPTION OF REFERENCE NUMERALS

1 Fuel tank as a gas storage device
2 Pressure-resistant container
3 Gas storage space
4 Storage material
5 Outlet
6 Inlet
7 Valve

The invention claimed is:

1. A metal complex comprising:
two different dicarboxylic acid compounds (I-1) and (I-2) each of which is a dicarboxylic acid compound (I) of formula (I),

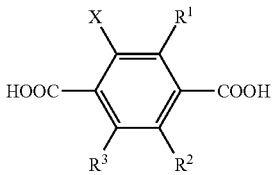

(I)

wherein
X is a hydrogen atom, an alkyl group that may have a substituent, an alkoxy group, a formyl group, an acyloxy group, an alkoxycarbonyl group, a nitro group, an amino group, a monoalkyl amino group, a dialkyl amino group, an acylamino group, or a halogen atom,
R$^1$, R$^2$, and R$^3$ are the same or different, and are each independently a hydrogen atom, an alkyl group that may have a substituent, or a halogen atom, and
X of the dicarboxylic acid compound (I-1) is an electron-donating group, and X of the dicarboxylic acid compound (I-2) is an electron-withdrawing group;
at least one kind of metal ion selected from metal ions belonging to Group 2 and Groups 7 to 12 of the periodic table; and
an organic ligand capable of bidentate binding to the metal ion, wherein a molar ratio of the dicarboxylic acid compound (I-1) to the dicarboxylic acid compound (I-2) is from 20:80 to 99:1,
wherein the organic ligand capable of bidentate binding is at least one selected from the group consisting of 4,4'-bipyridyl, 2,2'-dimethyl-4,4'-bipyridine, 1,2-bis(4-pyridyl)ethyne, 1,4-bis(4-pyridyl)butadiyne, 1,4-bis(4-pyridyl)benzene, 3,6-di(4-pyridyl)-1,2,4,5-tetrazine, 2,2'-bi-1,6-naphthyridine, phenazine, diazapyrene, trans-1,2-bis(4-pyridyl)ethane, 4,4'-azopyridine, 1,2-bis(4-pyridyl)ethane, 4,4'-dipyridyl sulfide, 1,3-bis(4-pyridyl)propane, 1,2-bis(4-pyridyl)glycol, N-(4-pyridyl)isonicotinamide, 2,6-di(4-pyridyl)benzo[1,2-c: 4,5-c']dipyrrol-1,3,5,7(2H,6H)-tetrone, 4,4'-bis(4-pyridyl)biphenylene, and N,N'-di(4-pyridyl)-1,4,5,8-naphthalenetetracarboxydiimide.

2. The metal complex according to claim 1, wherein
X of the dicarboxylic acid compound (I-1) is an alkyl group that may have a substituent, an alkoxy group or hydrogen atom, and
X of the dicarboxylic acid compound (I-2) is a formyl group, a nitro group, a fluorine atom, a chlorine atom, a bromine atom, an iodine atom or a hydrogen atom, unless X of the dicarboxylic acid compound (I-1) and X of the dicarboxylic acid compound (I-2) are hydrogen atoms simultaneously.

3. The metal complex according to claim 1, wherein a combination of the dicarboxylic acid compound (I-1) and the dicarboxylic acid compound (I-2) is selected from the group consisting of 2-methoxyterephthalic acid and 2-nitroterephthalic acid, 2-methylterephthalic acid and 2-nitroterephthalic acid, 2-methoxyterephthalic acid and terephthalic acid, 2-methylterephthalic acid and terephthalic acid, terephthalic acid and 2-nitroterephthalic acid, terephthalic acid and 2-fluoroterephthalic acid, terephthalic acid and 2-chloroterephthalic acid, terephthalic acid and 2-bromoterephthalic acid, and terephthalic acid and 2-iodoterephthalic acid.

4. The metal complex according to claim 1, wherein the metal ion is a copper ion or a zinc ion.

5. The metal complex according to claim 1, wherein a ratio of the dicarboxylic acid compound (I) to the organic ligand capable of bidentate binding, both forming the metal complex, is 2:1.

6. An adsorbent material comprising the metal complex according to claim 1.

7. The adsorbent material according to claim 6, wherein the adsorbent material is an adsorbent material suitable for adsorbing carbon dioxide, hydrogen, carbon monoxide, oxygen, nitrogen, hydrocarbon having 1 to 4 carbon atoms, noble gas, hydrogen sulfide, ammonia, sulfur oxide, nitrogen oxide, siloxane, water vapor, or organic vapor.

8. A storage material comprising the metal complex according to claim 1.

9. The storage material according to claim 8, wherein the storage material is a storage material suitable for storing carbon dioxide, hydrogen, carbon monoxide, oxygen, nitrogen, hydrocarbon having 1 to 4 carbon atoms, noble gas, hydrogen sulfide, ammonia, water vapor, or organic vapor.

10. A gas storage device comprising a pressure-resistant container and a gas storage space inside the pressure-resistant container, wherein the pressure-resistant container can be made airtight and has an outlet and an inlet for a gas, and the storage material according to claim 8 is in the gas storage space.

11. A gas-fueled automobile, comprising an internal-combustion engine that obtains a driving force from a fuel gas supplied from the gas storage device according to claim 10.

12. A separating material, comprising the metal complex according to claim 1.

13. The separating material according to claim 12, wherein the separating material is a separating material suitable for separating carbon dioxide, hydrogen, carbon monoxide, oxygen, nitrogen, hydrocarbon having 1 to 4 carbon atoms, noble gas, hydrogen sulfide, ammonia, sulfur oxide, nitrogen oxide, siloxane, water vapor, or organic vapor.

14. The separating material according to claim 12, wherein the separating material is a separating material suitable for separating methane and carbon dioxide, hydrogen and carbon dioxide, nitrogen and carbon dioxide, ethylene and carbon dioxide, methane and ethane, ethane and ethylene, propane and propene, ethylene and acetylene, nitrogen and methane, or air and methane.

15. A separation method, comprising separating with a separating material, by contacting a metal complex and a mixed gas in a pressure range from 0.01 MPa to 10 MPa, the separating material comprising the metal complex, the metal complex comprising:
two different dicarboxylic acid compounds (I-1) and (I-2) each of which is a dicarboxylic acid compound (I) of formula (I),

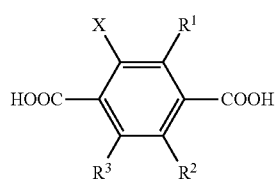

wherein
X is a hydrogen atom, an alkyl group that may have a substituent, an alkoxy group, a formyl group, an acyloxy group, an alkoxycarbonyl group, a nitro group, an amino group, a monoalkyl amino group, a dialkyl amino group, an acylamino group, or a halogen atom, $R^1$, $R^2$, and $R^3$ are the same or different, and are each independently a hydrogen atom, an alkyl group that may have a substituent, or a halogen atom, and X of the dicarboxylic acid compound (I-1) is an electron-donating group, and X of the dicarboxylic acid compound (I-2) is an electron-withdrawing group;

at least one kind of metal ion selected from metal ions belonging to Group 2 and Groups 7 to 12 of the periodic table; and an organic ligand capable of bidentate binding to the metal ion, wherein a molar ratio of the dicarboxylic acid compound (I-1) to the dicarboxylic acid compound (I-2) is from 20:80 to 99:1.

16. The separation method according to claim 15, wherein the separation method is a pressure swing adsorption process or a temperature swing adsorption process.

17. A method for producing the metal complex according to claim 1, comprising reacting, in a solvent, the dicarboxylic acid compound (I), the metal ion, and the organic ligand to precipitate the metal complex.

18. A metal complex comprising:
two different dicarboxylic acid compounds (I-1) and (I-2) each of which is a dicarboxylic acid compound (I) of formula (I),

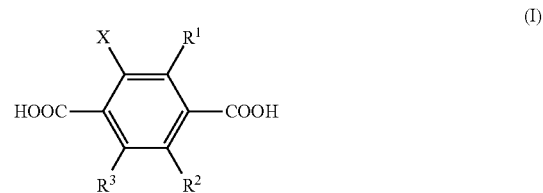

wherein
X is a hydrogen atom, an alkyl group that may have a substituent, an alkoxy group, a formyl group, an acyloxy group, an alkoxycarbonyl group, a nitro group, an amino group, a monoalkyl amino group, a dialkyl amino group, an acylamino group, or a halogen atom, $R^1$, $R^2$, and $R^3$ are the same or different, and are each independently a hydrogen atom, an alkyl group that may have a substituent, or a halogen atom, and X of the dicarboxylic acid compound (I-1) is an electron-donating group, and X of the dicarboxylic acid compound (I-2) is an electron-withdrawing group;

at least one kind of metal ion selected from metal ions belonging to Group 2 and Groups 7 to 12 of the periodic table; and an organic ligand capable of bidentate binding to the metal ion, wherein a molar ratio of the dicarboxylic acid compound (I-1) to the dicarboxylic acid compound (I-2) is from 20:80 to 99:1, wherein a combination of the dicarboxylic acid compound (I-1) and the dicarboxylic acid compound (I-2) is selected from the group consisting of 2-methoxyterephthalic acid and 2-nitroterephthalic acid, 2-methylterephthalic acid and 2-nitroterephthalic acid, 2-methoxyterephthalic acid and terephthalic acid, 2-methylterephthalic acid and terephthalic acid, terephthalic acid and 2-nitroterephthalic acid, terephthalic acid and 2-fluoroterephthalic acid, terephthalic acid and 2-chloro terephthalic acid, terephthalic acid and 2-bromoterephthalic acid, and terephthalic acid and 2-iodoterephthalic acid.

\* \* \* \* \*